(12) United States Patent
Wang et al.

(10) Patent No.: US 10,730,851 B2
(45) Date of Patent: Aug. 4, 2020

(54) POLYMORPH OF TRIARYLDIMETHYLPIPERAZINE DIHYDROCHLORIDE AND PREPARATION METHOD AND APPLICATION THEREOF

(71) Applicant: Yunnan Institute of Materia Medica, Kunming (CN)

(72) Inventors: Jingkun Wang, Kunming (CN); Zhaoyun Zhu, Kunming (CN); He Song, Kunming (CN); Min Sun, Kunming (CN); Tao Cui, Kunming (CN); Zeren Wang, Kunming (CN); Zhi Yang, Kunming (CN); Min Su, Kunming (CN); Hongbin Liu, Kunming (CN); Bing Shi, Kunming (CN); Yong Mao, Kunming (CN); Huilang Liu, Kunming (CN); Zeqian Li, Kunming (CN); Chunmei Zhao, Kunming (CN); Mei Su, Kunming (CN); Fang Yuan, Kunming (CN); Tiancai Zhang, Kunming (CN); Yong Liu, Kunming (CN); Kuanren Zhang, Kunming (CN); Yunlin Wei, Kunming (CN); Yuehai Shen, Kunming (CN)

(73) Assignee: Yunnan Institute of Materia Medica, Kunming (CN)

( * ) Notice: Subject to any disclaimer, the term of this patent is extended or adjusted under 35 U.S.C. 154(b) by 0 days.

(21) Appl. No.: 16/344,959

(22) PCT Filed: Nov. 21, 2016

(86) PCT No.: PCT/CN2016/106561
§ 371 (c)(1),
(2) Date: Apr. 25, 2019

(87) PCT Pub. No.: WO2018/090360
PCT Pub. Date: May 24, 2018

(65) Prior Publication Data
US 2019/0270720 A1    Sep. 5, 2019

(51) Int. Cl.
| C07D 401/10 | (2006.01) |
| A61P 25/24 | (2006.01) |
| A61P 1/04 | (2006.01) |
| A61P 9/10 | (2006.01) |
| A61P 29/00 | (2006.01) |
| A61K 31/496 | (2006.01) |
| A61P 25/04 | (2006.01) |

(52) U.S. Cl.
CPC .......... *C07D 401/10* (2013.01); *A61K 31/496* (2013.01); *A61P 1/04* (2018.01); *A61P 9/10* (2018.01); *A61P 25/04* (2018.01); *A61P 25/24* (2018.01); *A61P 29/00* (2018.01); *C07B 2200/13* (2013.01)

(58) Field of Classification Search
CPC .................................................. C07D 401/10
See application file for complete search history.

(56) References Cited

FOREIGN PATENT DOCUMENTS

| CN | 101318952 A | 12/2008 |
| CN | 104592184 A | 5/2015 |
| CN | 106588872 A | 4/2017 |
| CN | 106588874 A | 4/2017 |
| CN | 106588875 A | 4/2017 |
| CN | 106588877 A | 4/2017 |

OTHER PUBLICATIONS

Aug. 17, 2017, International Search Report of PCT/CN2016/106561.

*Primary Examiner* — Brian E McDowell
(74) *Attorney, Agent, or Firm* — Banner & Witcoff, Ltd.

(57) ABSTRACT

The application discloses five polymorph forms B, P, F, J, O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, preparation methods thereof and application thereof in the manufacture of a medicament for preventing or treating a mood disorder or a disease related to a δ opioid receptor.

17 Claims, 12 Drawing Sheets

POLYMORPH OF TRIARYLDIMETHYLPIPERAZINE DIHYDROCHLORIDE AND PREPARATION METHOD AND APPLICATION THEREOF

CROSS-REFERENCE TO RELATED APPLICATIONS

The present application is a U.S. National Phase Entry of International PCT Application No. PCT/CN2016/106561 having an international filing date of Nov. 21, 2016. The present application claims priority and the benefit of the above-identified application and the above-identified application is incorporated by reference herein in its entirety.

TECHNICAL FIELD

The application relates to, but is not limited to, the technical field of medicine, in particular to, but is not limited to, a polymorph form of triaryldimethylpiperazine dihydrochloride and a preparation method and application thereof.

BACKGROUND

Depression is a common mental disease, mainly manifested as feeling down, reduced interest, pessimism, slow thinking, lack of initiative, self-accusation and self-guilty, poor diet and sleep, fear of suffering from various diseases, feeling unwell in many parts of the body, and suicidal thoughts and behaviors in serious cases. In the fourth edition of "Diagnostic and Statistical Manual of Mental Disorders" published by the American Psychiatric Association, the depression is classified into three types: a severe depression, a dysthymia disorder and other unspecified depressions.

Factors causing depressions include: genetic factors, physical factors, central nervous medium functions and metabolic abnormalities, mental factors, etc. In efforts to treat the depressions, various antidepressant compositions have been developed, such as sertraline, flosi, paroxetine, fluvoxamine, and bupropion. Although these drugs are effective, they often produce problematic side effects, such as narcolepsy, confusion, inability to concentrate and sexual dysfunction. Moreover, these drugs have the problem of long onset time, which requires about 6 to 8 weeks to show any desired therapeutic effect.

SUMMARY OF THE INVENTION

The following is an overview of the subject matters described in detail herein. This summary is not intended to limit the scope of protection of the claims.

According to a large number of experimental researches, the inventor of the application discovers that triaryldimethylpiperazine compounds can enhance the action of opioid receptors in anti-depression from different ways, and therefore, based on the opioid receptor δ-receptor theory, according to the specific position of the anti-depression activity δ-receptor and aiming at the action target δ-receptor of depression, a triaryldimethylpiperazine compound (4-((R)-((2 S),5R)-4-(3-fluorobenzyl)-(2,5-dimethylpiperazine-1-yl)(3-hydroxyphenyl)methyl)phenyl)(4-methylpiperidine-1-yl)methanone dihydrochloride (molecular formula: $C_{33}H_{42}FCl_2N_3O_2$, molecular weight: 602.69) and its polymorph forms are developed, and intended to develop it into new drug components with antidepressant effect and other potential effects.

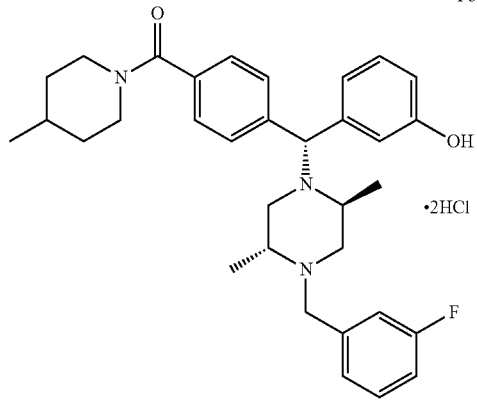

Formula I

An embodiment of the invention provides five polymorph forms of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, namely a polymorph form B, polymorph form F, polymorph form P, polymorph form J and polymorph form O.

An embodiment of the invention also provides preparation methods of a polymorph form B, polymorph form F, polymorph form P, polymorph form J and polymorph form O of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride.

An embodiment of the invention also provides polymorph forms prepared by the preparation methods of the polymorph form B, the polymorph form F, the polymorph form P, the polymorph form J and the polymorph form O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride according to any one of embodiments of the invention.

An embodiment of the invention also provides a pharmaceutical composition including at least one of the polymorph form B, the polymorph form F, the polymorph form P, the polymorph form J and the polymorph form O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride according to any one of embodiments of the invention.

An embodiment of the invention also provides use of the polymorph form B, the polymorph form F, the polymorph form P, the polymorph form J or the polymorph form O of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride according to any one of embodiments of the invention.

An embodiment of the invention provides a polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, wherein an X-ray powder diffraction pattern of the polymorph form B includes the following diffraction peaks at 2θ value: 17.6±0.2°, 8.0±0.2°, 23.6±0.2°, 13.0±0.2° and 9.2±0.2°.

In one embodiment, the X-ray powder diffraction pattern of the polymorph form B further includes any one or more of diffraction peaks at 2θ value selected from 19.8±0.2°, 15.6±0.2°, 14.6±0.2°, 25.4±0.2°, 11.7±0.2°, 26.7±0.2°, 19.4±0.2°, 22.5±0.2°, 16.8±0.2° and 18.4±0.2°.

In one embodiment, the melting point of the polymorph form B measured by differential scanning calorimetry is in the range of 154.4° C. to 171.6° C., optionally being about 171.6° C.

In some embodiments, the polymorph form B has the XRPD pattern shown in FIG. 1 and TGA and DSC patterns shown in FIG. 2.

The embodiment of the invention provides a preparation method of a polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride including:

adding a solvent to (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone, then adding concentrated hydrochloric acid solution, stirring until no solid precipitates, filtering, and drying to obtain the polymorph form B, the solvent being selected from a group consisting of any one or more of acetone, methyl isobutyl ketone, methyl isopropyl ketone, cyclohexane, methylcyclohexane, n-hexane, petroleum ether, ethyl ether, methyl tert-butyl ether, 1,4-dioxane, methyl ethyl ketone, methyl isobutyl ketone, and methyl pyrrolidone, or of any one or more of ethyl acetate, butyl acetate, ethyl formate, isobutyl acetate, isopropyl acetate, methyl acetate and propyl acetate.

In one embodiment, for 10 g of the (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone, the amount of the solvent added is 50 mL to 1000 mL, optionally 50 mL to 300 mL, and the amount of the concentrated hydrochloric acid solution added is 1.5 mL to 7.0 mL, optionally 1.75 mL to 5.25 mL; the stirring is carried out in the range of 10° C. to 40° C.; the time for stirring is 0.5 h to 12 h, optionally 2 h to 4 h.

The embodiment of the invention provides a polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, an X-ray powder diffraction pattern of the polymorph form F includes the following diffraction peaks at 2θ value: 23.7±0.2°, 14.6±0.2°, 11.8±0.2°, 13.0±0.2° and 17.2±0.2°.

In one embodiment, the X-ray powder diffraction pattern of the polymorph form F further includes any one or more of diffraction peaks at 2θ value selected from 27.8±0.2°, 13.4±0.2°, 19.7±0.2°, 8.7±0.2°, 7.8±0.2°, 26.2±0.2°, 15.7±0.2°, 21.5±0.2° and 9.4±0.2°.

In one embodiment, the melting point of the polymorph form F measured by differential scanning calorimetry is in the range of 179.1° C. to 185.9° C., optionally being about 185.9° C.

In some embodiments, the polymorph form F has an XRPD pattern shown in FIG. 3 and TGA and DSC patterns shown in FIG. 4.

The embodiment of the invention provides a preparation method of a polymorph form F of (4-((R)-((2S,5R)-4-(3-fluorobenzyl)-(2,5-dimethylpiperazine-1-yl)(3-hydroxyphenyl)methyl)phenyl) (4-methylpiperidine-1-yl)methanone dihydrochloride including:

(1) adding a solvent to the polymorph form B of any one of embodiments, so that the polymorph form B is completely dissolved, stirring until solid precipitates, and separating the solid to obtain the polymorph form F; or (2) adding a solvent to the polymorph form B of any one of embodiments, so that the polymorph form B is completely dissolved, slowly volatilizing the obtained solution until solid precipitates, and collecting the solid to obtain the polymorph form F; or (3) hermetically placing the polymorph form B of any one of embodiments in an atmosphere containing a solvent, to obtain the polymorph form F through liquid-solid gas phase infiltration, wherein, in methods (1) to (3), the solvent is selected from a group consisting of any one or more of methanol, ethanol, propanol, ethoxyethanol, 2-methoxyethanol, 1-butanol, 2-butanol, 3-methyl-1-butanol, 2-methyl-1-propanol, 1-pentanol, 1-propanol, 2-propanol, and propylene glycol, or a mixed solvent of any one or more thereof with water.

In one embodiment, in method (1), for 1.5 g of the polymorph form B, the amount of the solvent added is 100 mL to 1000 mL, optionally 100 mL to 300 mL; the stirring until the solid precipitates is carried out in the range of 40° C. to 60° C., and the time for the stirring is 0.5 h to 12 h, and optionally 2 h to 4 h.

In one embodiment, in method (2), for 1.5 g of the polymorph form B, the amount of the solvent added is 100 mL to 1000 mL, optionally 100 mL to 300 mL; and the obtained solution is slowly volatilized at room temperature until the solid precipitates.

In one embodiment, in method (3), the polymorph form B is hermetically placed in an atmosphere containing the solvent at room temperature for 1 to 7 days, optionally 5 days.

The embodiment of the invention provides a polymorph form P of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride, an X-ray powder diffraction pattern of the polymorph form P includes the following diffraction peaks at 2θ value: 10.0±0.2°, 9.1±0.2°, 21.3±0.2°, 22.6±0.2° and 14.5±0.2°.

In one embodiment, the X-ray powder diffraction pattern of the polymorph form P further includes any one or more of diffraction peaks at 2θ value selected from 17.7±0.2°, 20.8±0.2°, 13.8±0.2°, 23.1±0.2°, 24.9±0.2°, 27.0±0.2°, 27.8±0.2°, 18.4±0.2°, 12.7±0.2°, 16.6±0.2°, 31.1±0.2°, 11.5±0.2° and 28.2±0.2°.

In one embodiment, the melting point of the polymorph form P measured by differential scanning calorimetry is in the range of 180.7° C. to 188.5° C., optionally being about 188.5° C.

In some embodiments, wherein the polymorph form P has an XRPD pattern shown in FIG. 5 and TGA and DSC patterns shown in FIG. 6.

The embodiment of the invention provides a preparation method of a polymorph form P of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride including:

(1) adding a solvent to (4-((R)-((2S,5R)-4-(3-fluorobenzyl)-(2,5-dimethylpiperazine-1-yl) (3-hydroxyphenyl)methyl)phenyl) (4-methylpiperidine-1-yl)methanone, then adding concentrated hydrochloric acid solution, stirring until no solid precipitates, filtering and drying to obtain the polymorph form P; or (2) adding a solvent to the polymorph form B of any one of embodiments, stirring until the dissolution equilibrium is reached, and separating solid to obtain the polymorph form P; or (3) adding a solvent to the polymorph form F of any one of claims 7 to 10 to obtain a suspension, stirring until the dissolution equilibrium is reached, separating solid to obtain the polymorph form P, wherein, in methods (1) to (3), the solvent is selected from a group consisting of any one or more of acetonitrile, dimethylformamide, diethylacetamide, formamide, dichloromethane, dimethylsulfoxide, and tetrahydrofuran, a mixed solvent of dimethylsulfoxide with water, or a mixed solvent of dimethylformamide with water.

In one embodiment, the method (1) further includes the step of adding the polymorph form P as a seed crystal to the reaction after adding concentrated hydrochloric acid solution.

In one embodiment, the mass of the polymorph form P serving as a seed crystal is 1% to 20% of the mass of (4-((R)-((2S,5R)-4-(3-fluorobenzyl)-(2,5-dimethylpiperazine-1-yl)(3-hydroxyphenyl)methyl)phenyl) (4-methylpiperidine-1-yl)methanone.

In one embodiment, in method (1), for 10 g of the (4-((R)-((2S,5R)-4-(3-fluorobenzyl)-(2,5-dimethylpiperazin-1-yl)(3-hydroxyphenyl)methyl)phenyl) (4-methylpiperidine-1-yl)methanone, the amount of solvent added is 50 mL to 1000 mL, optionally 50 mL to 300 mL, and the amount of the concentrated hydrochloric acid solution added is 1.5 mL to 7.0 mL, optionally 1.75 mL to 7.0 ml, the stirring is carried out in the range of 40° C. to 60° C.; the time for stirring is 0.5 h to 12 h, optionally 2 h to 4 h.

In one embodiment, in method (2), for 1.5 g of the polymorph form B, the amount of solvent added is 20 mL to 500 mL, optionally 20 mL to 200 mL; the stirring reaction is carried out in the range of 40° C. to 60° C., optionally 50° C., and the stirring reaction is carried out for 1 h to 12 h, optionally 2 h to 4 h.

In one embodiment, in method (3), for 1.5 g of the polymorph form F, the amount of solvent added is 50 mL to 1000 mL, optionally 20 mL to 500 mL; the stirring reaction is carried out in the range of 10° C. to 40° C., optionally 15° C. to 30° C., and the time for the stirring reaction is 1 h to 5 days, optionally 3 h to 4 days.

The embodiment of the invention provides a polymorph form J of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride, an X-ray powder diffraction pattern of the polymorph form J includes the following diffraction peaks at 2θ value: 16.8±0.2°, 23.3±0.2°, 12.8±0.2°, 11.4±0.2° and 17.1±0.2°.

In one embodiment, the X-ray powder diffraction pattern of the polymorph form J further includes any one or more of diffraction peaks at 2θ value selected from 27.2±0.2°, 11.6±0.2°, 25.4±0.2°, 22.3±0.2°, 13.2±0.2°, 19.1±0.2°, 8.6±0.2°, 13.9±0.2°, 19.4±0.2°, 9.2±0.2°, 27.8±0.2°, 21.3±0.2°, 23.8±0.2° and 28.8±0.2°.

In one embodiment, the melting point of the polymorph form J measured by differential scanning calorimetry is in the range of 175.7° C. to 182.5° C., optionally being about 182.5° C.

In some embodiments, the polymorph form J has an XRPD pattern shown in FIG. 7 and TGA and DSC patterns shown in FIG. 8.

The embodiment of the invention provides a preparation method of a polymorph form J of (4-((R)-((2S,5R)-4-(3-fluorobenzyl)-(2,5-dimethylpiperazine-1-yl) (3-hydroxyphenyl)methyl)phenyl) (4-methylpiperidine-1-yl)methanone dihydrochloride including:

(1) hermetically placing the polymorph form B of any one of embodiments in an atmosphere containing water vapor, to obtain the polymorph form J through liquid-solid gas phase infiltration; or (2) grinding the polymorph form B of any one of embodiments directly or in the presence of trace amount of water, and standing for 1 to 10 days to obtain the polymorph form J.

In one embodiment, in the method (1), the polymorph form B is hermetically placed in an atmosphere containing water vapor and standed at room temperature for 1 to 7 days, optionally 5 days.

In one embodiment, in method (2), the grinding is performed for 5 min to 60 min, optionally 10 min; the obtained solid is standed at room temperature and a relative humidity of 80% to 97.3% for 1 to 10 days, optionally 8 days.

Embodiments of the present invention provide a polymorph form O of (4-((R)-((2S,5R)-4-(3-fluorobenzyl)-(2,5-dimethylpiperazine-1-yl) (3-hydroxyphenyl)methyl)phenyl) (4-methylpiperidine-1-yl)methanone dihydrochloride, an X-ray powder diffraction pattern of the polymorph form O includes the following diffraction peaks at 2θ value: 23.1±0.2°, 17.0±0.2°, 12.8±0.2°, 11.4±0.2° and 22.0±0.2°.

In one embodiment, the X-ray powder diffraction pattern of the polymorph form O further includes any one or more of diffraction peaks at 2θ value selected from 27.0±0.2°, 25.8±0.2°, 14.0±0.2°, 18.6±0.2°, 21.0±0.2°, 8.7±0.2° and 28.4±0.2°.

In one embodiment, the melting point of the polymorph form O measured by differential scanning calorimetry is in the range of 175.0° C. to 183.6° C., optionally being about 183.6° C.

In some embodiments, the polymorph form O has the XRPD pattern shown in FIG. 9 and TGA and DSC patterns shown in FIG. 10.

A preparation method of a polymorph form O of (4-((R)-((2S,5R)-4-(3-fluorobenzyl)-(2,5-dimethylpiperazine-1-yl) (3-hydroxyphenyl)methyl)phenyl) (4-methylpiperidine-1-yl)methanone dihydrochloride includes:

heating the polymorph form J of any one of embodiments to a temperature in the range of 80° C. to 120° C., optionally in the range of 90° C. to 110° C., and naturally cooled under the protection of inert gas, optionally nitrogen, to obtain the polymorph form O.

The embodiment of the invention provides a pharmaceutical composition including at least one of the polymorph form B of any one of embodiments or the polymorph form B obtained by the preparation method of any one of embodiments, the polymorph form F of any one of embodiments or the polymorph form F obtained by the preparation method of any one of embodiments, the polymorph form P of any one of embodiments or the polymorph form P obtained by the preparation method of any one of embodiments, the polymorph form J of any one of embodiments or the polymorph form J obtained by the preparation method of any one of embodiments, and the polymorph form O of any one of embodiments or the polymorph form O obtained by the preparation method of embodiments.

In some embodiments of the invention, the pharmaceutical composition may further include pharmaceutically acceptable carriers or excipients, the excipients may be conventional functional excipients, such as fillers (e.g., starch or sugars, etc.), binders (e.g., microcrystalline cellulose, etc.), dispersants (e.g., anhydrous calcium phosphate, precipitated calcium carbonate, calcium silicate, etc.). Optionally, the filler is mannitol.

In some embodiments of the invention, the pharmaceutical composition can be made into solid oral preparations, such as tablets, pills, capsules or powders.

An embodiment of the invention provide use of the polymorph form B of any one of embodiments or the polymorph form B obtained by the preparation method of any one of embodiments, the polymorph form F of any one of embodiments or the polymorph form F obtained by the preparation method of any one of embodiments, the polymorph form P of any one of embodiments or the polymorph form P obtained by the preparation method of any one of embodiments, the polymorph form J of any one of embodiments or the polymorph form J obtained by the preparation method of any one of embodiments, and the polymorph form O of any one of embodiments or the polymorph form O obtained by the preparation method of any one of embodiments in the manufacture of a medicament for preventing or treating a mood disorder or a disease related to a δ opioid receptor.

An embodiment of the invention simultaneously provides use of (4-((R)-((2S,5R)-4-(3-fluorobenzyl)-(2,5-dimethyl-piperazine-1-yl) (3-hydroxyphenyl)methyl)phenyl)(4-methylpiperidine-1-yl)methanone and pharmaceutically acceptable salts thereof (e.g., dihydrochloride) in the manufacture of medication for preventing or treating a mood disorder or a disease related to a δ opioid receptor.

In some embodiments of the present invention, the mood disorder may be depression; diseases related to δ opioid receptors may be anxiety, pain, ischemia-hypoxia/reperfusion injury or colitis, optionally ulcerative colitis, etc.

According to the embodiments of the invention, five polymorph forms B, P, F, J and O of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride are prepared by methods such as slow volatilization crystallization at room temperature, suspension stirring, slow cooling, liquid-solid gas phase infiltration or wet grinding. The five polymorph forms have high solubility, good absorption, high bioavailability, low toxicity and good stability, which can effectively prevent and treat depression and other potential diseases, and are suitable for the development and industrial production of new drugs.

Other aspects will become apparent upon reading and understanding the drawings and detailed description.

BRIEF DESCRIPTION OF DRAWINGS

The accompanying drawings are intended to provide a further understanding of the embodiments of the invention and form a part of the specification. Together with the following detailed description, they are used to explain the embodiments of the invention, but are not intended to limit the embodiments of the invention. In the drawings.

DETAILED DESCRIPTION OF THE PREFERRED EMBODIMENT

Hereinafter, specific embodiments of the invention will be described in detail. It should be understood that the specific embodiments described herein are only for the purpose of illustrating and explaining the invention and are not intended to limit the invention.

The invention will be further described below with reference to the Examples of the invention. Unless otherwise specified, the reagents and raw materials used in the Examples of the invention are all commercially available. In different Examples, the same reagent sources are the same.

X-Ray Powder Diffraction

The X-ray powder diffraction (XRPD) pattern of the embodiment of the invention is collected on a PANalytical (Panako) Empyrean X-ray powder diffraction analyzer, and XRPD parameters are as follows:

| Parameter | Reflection parameter |
|---|---|
| X ray | Cu, kα, Kα1 (Å): 1.540598; Kα2 (Å): 1.544426 Kα2/Kα1 strength ratio: 0.50 |
| X-ray tube setting | 45 kV, 40 mA |
| Divergent slit | Automatic |

-continued

| Parameter | Reflection parameter |
|---|---|
| monochromator | No |
| Scanning mode | Continuous |
| Scanning range (°2θ) | 3°~40° |
| Scanning step size (°2θ) | 0.017 |
| Scanning time (min) | 3'56' |

Thermogravimetry and Differential Scanning Calorimetry

The thermogravimetric analysis (TGA) pattern and differential scanning calorimetry (DSC) pattern of the embodiments of the invention are respectively collected on a TA Q500 thermogravimetric analyzer and a TA Q200 differential scanning calorimeter, and the experimental parameters are as follows:

| Parameter | TGA settings | DSC settings |
|---|---|---|
| Sample tray | Platinum plate, open | Aluminum plate, gland |
| Temperature range/° C. | RT-360° C. | RT-400° C. |
| Scanning rate/° C./min | 10 | 10 |
| shielding gas | Nitrogen | Nitrogen |

Example 1 Preparation of a Polymorph Form B of (4-((R)-((2S, 5R)-4-(3-fluorobenzyl)-(2,5-dimethyl-piperazine-1-yl)(3-hydroxyphenyl)methyl) phenyl)(4-methylpiperidine-1-yl)methanone dihydrochloride 10 g of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone is added into a glass bottle, 200 mL of acetone is added into the glass bottle, and stirred uniformly. Then 3.5 mL of concentrated hydrochloric acid solution with a volume percentage of 37.5% is added, stirred at room temperature, reacted for 3 h, filtered, and dried under vacuum, so that the polymorph form B of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride is obtained.

Figure 1:
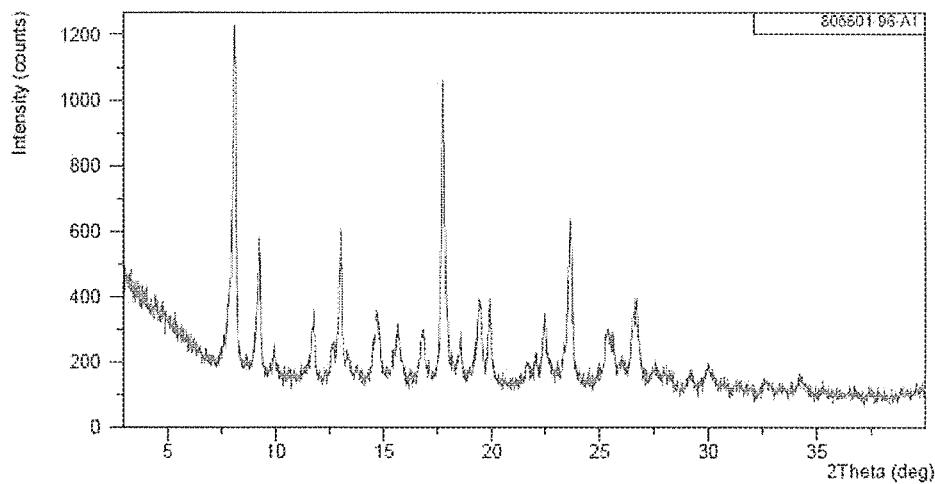
FIG. 1 is an XRPD pattern of a polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.
Figure 2:
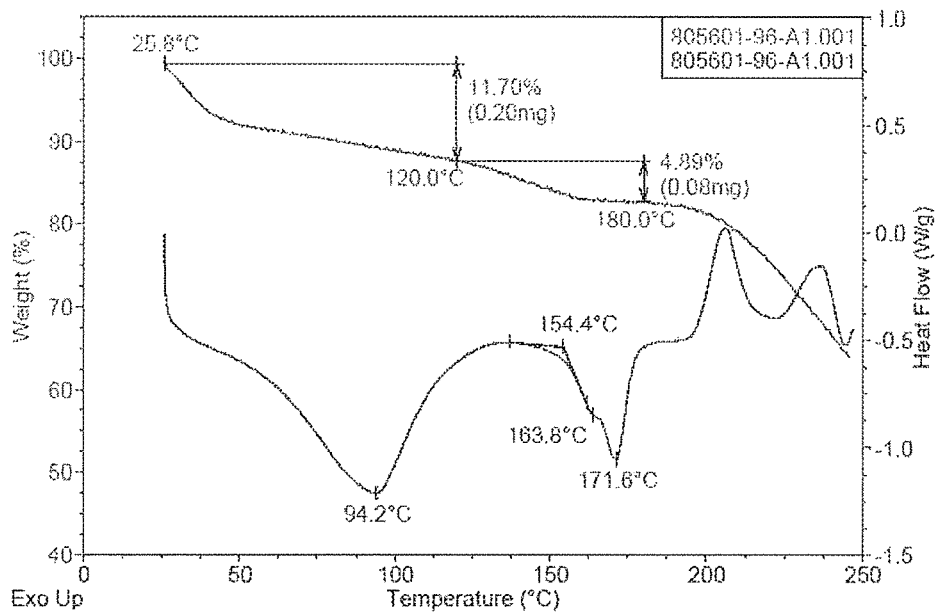
FIG. 2 is TGA and DSC patterns of a polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.

The XRPD pattern of the polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method is shown in FIG. 1, and the peak information of the pattern is shown in Table 1. The TGA and DSC patterns of the polymorph form B are shown in FIG. 2. As can be seen from FIG. 2, the melting point of the polymorph form B is 171.6° C. (the melting range is 154.4° C. to 171.6° C. as judged by DSC).

TABLE 1

XRPD peak information of polymorph form B

| Position [°2θ] | Height [cts] | Left half-height width [°2θ] | Face distance [Å] | Relative strength [%] |
|---|---|---|---|---|
| 8.04 | 1918.6 | 0.10 | 11.0 | 59.2 |
| 9.19 | 879.2 | 0.13 | 9.6 | 27.1 |
| 11.75 | 576.0 | 0.10 | 7.5 | 17.8 |

TABLE 1-continued

XRPD peak information of polymorph form B

| Position [°2θ] | Height [cts] | Left half-height width [°2θ] | Face distance [Å] | Relative strength [%] |
|---|---|---|---|---|
| 12.96 | 1029.0 | 0.12 | 6.8 | 31.8 |
| 14.60 | 649.1 | 0.13 | 6.1 | 20.0 |
| 15.59 | 803.7 | 0.31 | 5.7 | 24.8 |
| 16.83 | 541.8 | 0.26 | 5.3 | 16.7 |
| 17.63 | 3240.5 | 0.12 | 5.0 | 100.0 |
| 18.44 | 472.8 | 0.31 | 4.8 | 14.6 |
| 19.41 | 565.8 | 0.26 | 4.6 | 17.5 |
| 19.82 | 871.0 | 0.13 | 4.5 | 26.9 |
| 22.51 | 546.5 | 0.18 | 3.9 | 16.9 |
| 23.61 | 1139.9 | 0.15 | 3.8 | 35.2 |
| 25.40 | 614.8 | 0.18 | 3.5 | 19.0 |
| 26.69 | 572.7 | 0.13 | 3.3 | 17.7 |
| 27.50 | 281.7 | 0.20 | 3.2 | 8.7 |
| 30.02 | 188.2 | 0.31 | 3.0 | 5.8 |
| 31.72 | 181.6 | 0.20 | 2.8 | 5.6 |
| 33.91 | 127.3 | 0.41 | 2.6 | 3.9 |

Example 2 Preparation of a Polymorph Form B of (4-((R)-((2S, 5R)-4-(3-fluorobenzyl)-(2,5-dimethyl-piperazine-1-yl)(3-hydroxyphenyl)methyl)phenyl)(4-methylpiperidine-1-yl)methanone dihydrochloride With reference to Example 1, Example 2 is different from Example 1 in that 200 mL of acetone added in Example 1 is replaced with 200 mL of ethyl acetate, and the other operations are the same as Example 1 to prepare the polymorph form B of (4-((R)-((2 S,5R)-4-(3-fluorobenzyl)-(2,5-dimethylpiperazine-1-yl) (3-hydroxyphenyl)methyl)phenyl)(4-methylpiperidine-1-yl)methanone dihydrochloride.

The XRPD, TGA and DSC patterns of the polymorph form B of (4-((R)-((2 S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 1 and 2, respectively.

Example 3 Preparation of a Polymorph Form F of (4-((R)-((2S, 5R)-4-(3-fluorobenzyl)-(2,5-dimethyl-piperazine-1-yl)(3-hydroxyphenyl)methyl)phenyl)(4-methylpiperidine-1-yl)methanone dihydrochloride 1.5 g of the polymorph form B of (4-((R)-((2 S,5R)-4-(3-fluorobenzyl)-(2,5-dimethylpiperazine-1-yl)(3-hydroxyphenyl)methyl)phenyl)(4-methylpiperidine-1-yl)methanone dihydrochloride of Example 1 is used as an initial sample, 100 mL of methanol is added to completely dissolve the polymorph form B sample in methanol to obtain a clear solution, stirred at 50° C. for 3 h, and the solid is separated to obtain the polymorph form F.

Figure 3:
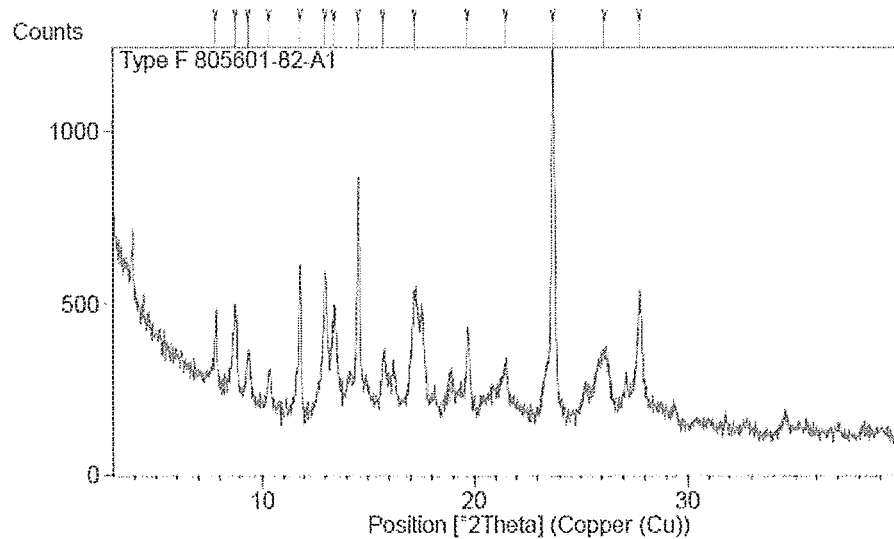
FIG. 3 is an XRPD pattern of a polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.
Figure 4:
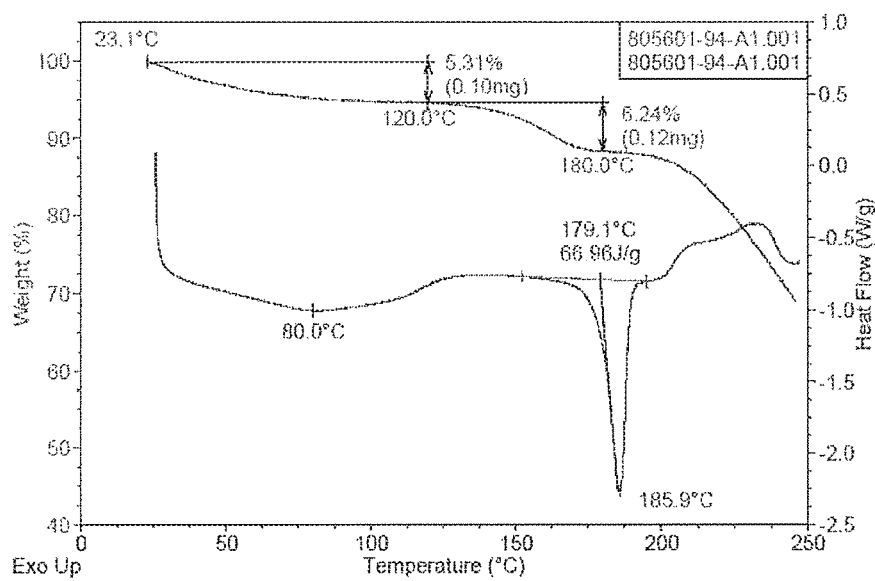
FIG. 4 is TGA and DSC patterns of a polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.

The XRPD pattern of the polymorph form F of (4-((R)-((2 S,5R)-4-(3-fluorobenzyl)-(2,5-dimethylpiperazine-1-yl)(3-hydroxyphenyl)methyl)phenyl)(4-methylpiperidine-1-yl) methanone dihydrochloride prepared according to the above method is shown in FIG. 3, and the peak information of the pattern is shown in Table 2. The TGA and DSC patterns of the polymorph form F are shown in FIG. 4. As can be seen from FIG. 4, the melting point of the polymorph form F is 185.9° C. (the melting range is 179.1° C. to 185.9° C. as judged by DSC).

TABLE 2

XRPD peak information of polymorph form F

| Position [°2θ] | Height [cts] | Left half-height width [°2θ] | Face distance [Å] | Relative strength [%] |
|---|---|---|---|---|
| 7.84 | 210.9 | 0.10 | 11.3 | 20.2 |
| 8.75 | 223.0 | 0.18 | 10.1 | 21.4 |
| 9.355 | 122.0 | 0.20 | 9.5 | 11.7 |
| 10.34 | 93.9 | 0.20 | 8.6 | 9.0 |
| 11.804 | 397.3 | 0.12 | 7.5 | 38.1 |
| 13.01 | 387.8 | 0.15 | 6.8 | 37.2 |
| 13.42 | 282.6 | 0.15 | 6.6 | 27.1 |
| 14.57 | 620.0 | 0.09 | 6.1 | 59.5 |
| 15.73 | 170.1 | 0.20 | 5.6 | 16.3 |
| 17.20 | 338.1 | 0.20 | 5.2 | 32.4 |
| 19.70 | 245.4 | 0.15 | 4.5 | 23.6 |
| 21.50 | 142.1 | 0.26 | 4.1 | 13.6 |
| 23.73 | 1042.4 | 0.14 | 3.7 | 100.0 |
| 26.15 | 178.6 | 0.51 | 3.4 | 17.1 |
| 27.78 | 336.4 | 0.18 | 3.2 | 32.3 |

Example 4 Preparation of a Polymorph Form F of (4-((R)-((2S, 5R)-4-(3-fluorobenzyl)-(2,5-dimethyl-piperazine-1-yl)(3-hydroxyphenyl)methyl) phenyl) (4-methylpiperidine-1-yl)methanone dihydrochloride 1.5 g of the polymorph form B of the (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride of Example 1 is used as an initial sample, 200 mL of methanol is added to completely dissolve the polymorph form B sample in methanol to obtain a clear solution, the obtained solution is slowly volatilized at room temperature, and the collected solid is the polymorph form F.

The XRPD, TGA and DSC patterns of the polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 3 and 4, respectively.

Example 5 Preparation of a Polymorph Form F of (4-((R)-((2S, 5R)-4-(3-fluorobenzyl)-(2,5-dimethyl-piperazine-1-yl)(3-hydroxyphenyl)methyl)phenyl)(4-methylpiperidine-1-yl)methanone dihydrochloride The polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride of Example 1 is taken as a starting sample and placed in an open glass bottle; the glass bottle is placed in a large glass bottle filled with methanol, and the glass bottle is sealed at room temperature for 5 days to obtain the polymorph form F.

The XRPD, TGA and DSC patterns of the polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 3 and 4, respectively.

Figure 5:
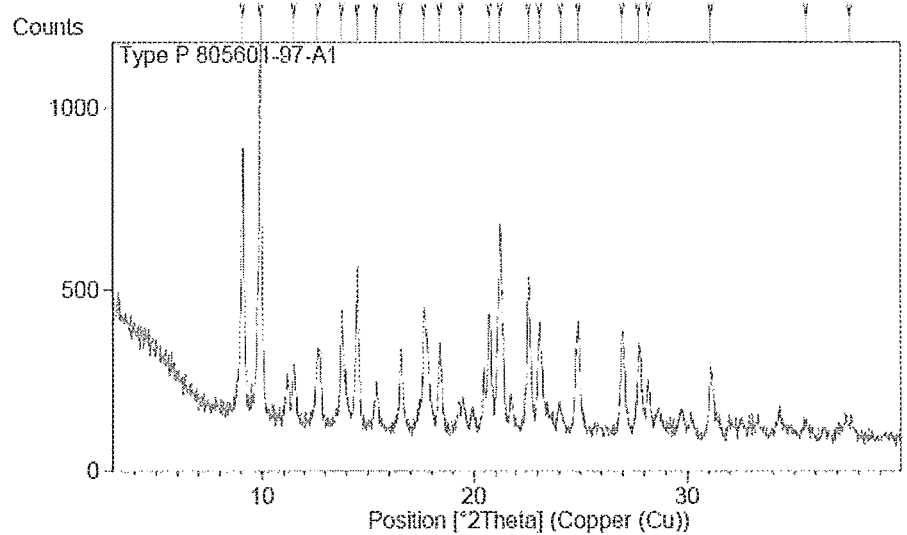
FIG. 5 is an XRPD pattern of a polymorph form P of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.
Figure 6:
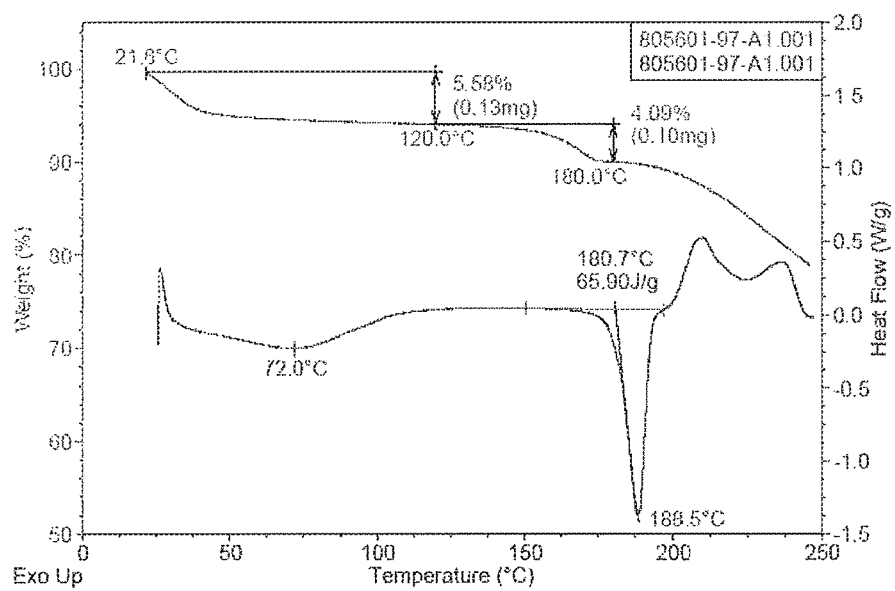
FIG. 6 is TGA and DSC patterns of a polymorph form P of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.

Example 6 Preparation of a Polymorph Form P of (4-((R)-((2S, 5R)-4-(3-fluorobenzyl)-(2,5-dimethyl-piperazine-1-yl)(3-hydroxyphenyl)methyl)phenyl) (4-methylpiperidine-1-yl)methanone dihydrochloride 10 g of (4-((R)-((2S, 5R)-4-(3-fluorobenzyl)-(2,5-dimethylpiperazine-1-yl) (3-hydroxyphenyl)methyl)phenyl) (4-methylpiperidine-1-yl)methanone into a 300 mL glass bottle, 100 mL acetonitrile is added into the glass bottle, stirred evenly. Then 3.5 mL concentrated hydrochloric acid solution with a volume percentage of 37.5% is added, stirred at room temperature, reacted for 3 h, filtered, dried under vacuum, so that the polymorph form P is obtained. The content determined by HPLC is no less than 96%. The XRPD pattern of the polymorph form P of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method is shown in FIG. 5, and the peak information of the pattern is shown in Table 3. The TGA and DSC patterns of the polymorph form P are shown in FIG. 6. As can be seen from FIG. 6, the melting point of the polymorph form P is 188.5° C. (the melting range is 180.7° C.-188.5° C. as judged by DSC).

TABLE 3

XRPD peak information of polymorph form P

| Position [°2θ] | Height [cts] | Left half-height width [°2θ] | Face distance [Å] | Relative strength [%] |
|---|---|---|---|---|
| 9.11 | 729.2 | 0.12 | 9.7 | 71.2 |
| 9.95 | 1023.6 | 0.12 | 8.9 | 100.0 |
| 11.51 | 147.6 | 0.13 | 7.7 | 14.4 |
| 12.68 | 195.6 | 0.20 | 7.0 | 19.1 |
| 13.80 | 300.3 | 0.10 | 6.4 | 29.3 |
| 14.50 | 397.4 | 0.13 | 6.1 | 38.8 |
| 15.40 | 96.2 | 0.15 | 5.8 | 9.4 |
| 16.57 | 194.1 | 0.13 | 5.38 | 19.0 |
| 17.66 | 308.6 | 0.10 | 5.08 | 30.2 |
| 18.40 | 216.3 | 0.13 | 4.88 | 21.1 |
| 19.41 | 54.3 | 0.31 | 4.6 | 5.3 |
| 20.75 | 306.8 | 0.13 | 4.3 | 30.0 |
| 21.25 | 539.6 | 0.28 | 4.2 | 52.8 |
| 22.57 | 403.4 | 0.13 | 3.9 | 39.4 |
| 23.08 | 280.4 | 0.20 | 3.9 | 27.4 |
| 24.08 | 53.4 | 0.31 | 3.7 | 5.2 |
| 24.91 | 275.8 | 0.18 | 3.6 | 26.9 |
| 26.98 | 272.1 | 0.15 | 3.3 | 26.6 |
| 27.76 | 231.9 | 0.18 | 3.2 | 22.7 |
| 28.21 | 118.0 | 0.15 | 3.2 | 11.5 |
| 31.10 | 169.7 | 0.13 | 2.9 | 16.6 |
| 35.56 | 31.8 | 0.41 | 2.5 | 3.1 |
| 37.55 | 40.0 | 0.72 | 2.4 | 3.9 |

Example 7 Preparation of a Polymorph Form P of (4-((R)-((2S, 5R)-4-(3-fluorobenzyl)-(2,5-dimethyl-piperazine-1-yl)(3-hydroxyphenyl)methyl)phenyl) (4-methylpiperidine-1-yl)methanone dihydrochloride 10 g of (4-((R)-((2S, 5R)-4-(3-fluorobenzyl)-(2,5-dimethylpiperazine-1-yl) (3-hydroxyphenyl)methyl)phenyl) (4-methylpiperidine-1-yl)methanone is added into a 300 mL glass bottle, 100 mL acetonitrile is added into the glass bottle, stirred uniformly. Then 3.5 mL concentrated hydrochloric acid solution with a volume percentage of 37.5% is added, and according to experimental requirements, the polymorph form P of Example 6, which is about 1% to 20% of the mass of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone, stirred at room temperature for 3 h, and dried under vacuum, so that the polymorph form P is obtained.

The XRPD, TGA and DSC patterns of the polymorph form P of (4-((R)-((2 S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 5 and 6, respectively.

Example 8 Preparation of a Polymorph Form P of (4-((R)-((2S, 5R)-4-(3-fluorobenzyl)-(2,5-dimethylpiperazine-1-yl)(3-hydroxyphenyl)methyl)phenyl)(4-methylpiperidine-1-yl)methanone dihydrochloride 1.5 g of the polymorph form B of Example 1 is weighed as a starting sample and placed into a 150 mL glass bottle, 35 mL acetonitrile is added to obtain a suspension, stirred at 50° C. for 3 h, and the solid is separated to obtain the polymorph form P.

The XRPD, TGA and DSC patterns of the polymorph form P of (4-((R)-((2 S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 5 and 6, respectively.

Example 9 Preparation of a Polymorph Form P of (4-((R)-((2S, 5R)-4-(3-fluorobenzyl)-(2,5-dimethylpiperazine-1-yl)(3-hydroxyphenyl) methyl)phenyl)(4-methylpiperidine-1-yl)methanone dihydrochloride 1.5 g of the polymorph form F of Example 3 is weighed as a starting sample and placed into a 150 mL glass bottle, 50 mL acetonitrile is added to obtain a suspension, stirred at room temperature for 4 h, and the solid is separated to obtain the polymorph form P.

The XRPD, TGA and DSC patterns of the polymorph form P of (4-((R)-((2S,5R)-4-(3-fluorobenzyl)-(2,5-dimethylpiperazine-1-yl) (3-hydroxyphenyl)methyl)phenyl)(4-methylpiperidine-1-yl)methanone dihydrochloride prepared according to the above method are the same as those of Figures. 5 and 6, respectively.

Example 10 Preparation of a Polymorph Form J of (4-((R)-((2S, 5R)-4-(3-fluorobenzyl)-(2,5-dimethylpiperazine-1-yl)(3-hydroxyphenyl)methyl)phenyl) (4-methylpiperidine-1-yl)methanone dihydrochloride The polymorph form B of (4-((R)-((2S,5R)-4-(3-fluorobenzyl)-(2,5-dimethylpiperazine-1-yl)(3-hydroxyphenyl) methyl)phenyl)(4-methylpiperidine-1-yl)methanone dihydrochloride of Example 1 is weighed as a starting sample, and placed in a glass bottle, the glass bottle is placed open in a large glass bottle filled with water, the large glass bottle is sealed at room temperature for 5 days, and the solid is taken out to obtain the polymorph form J.

Figure 7:
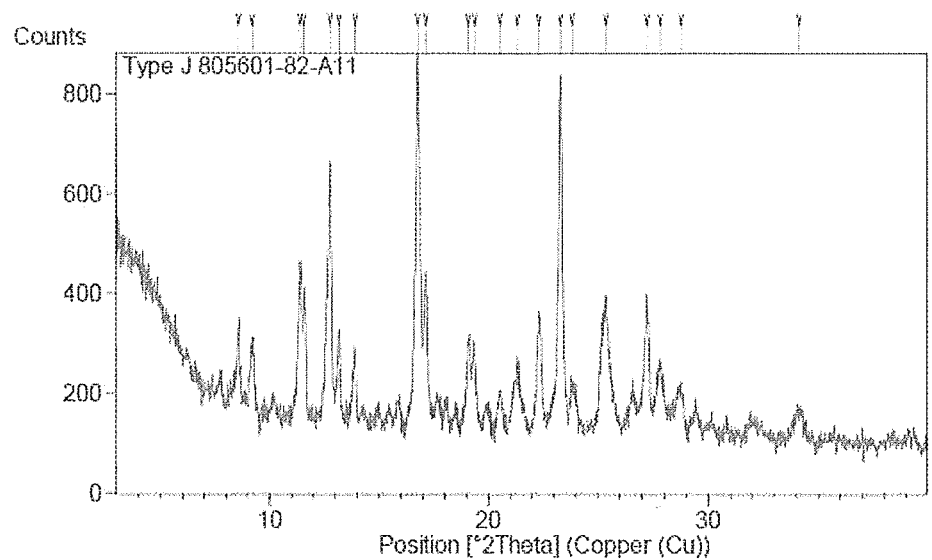
FIG. 7 is an XRPD pattern of a polymorph form J of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.
Figure 8:
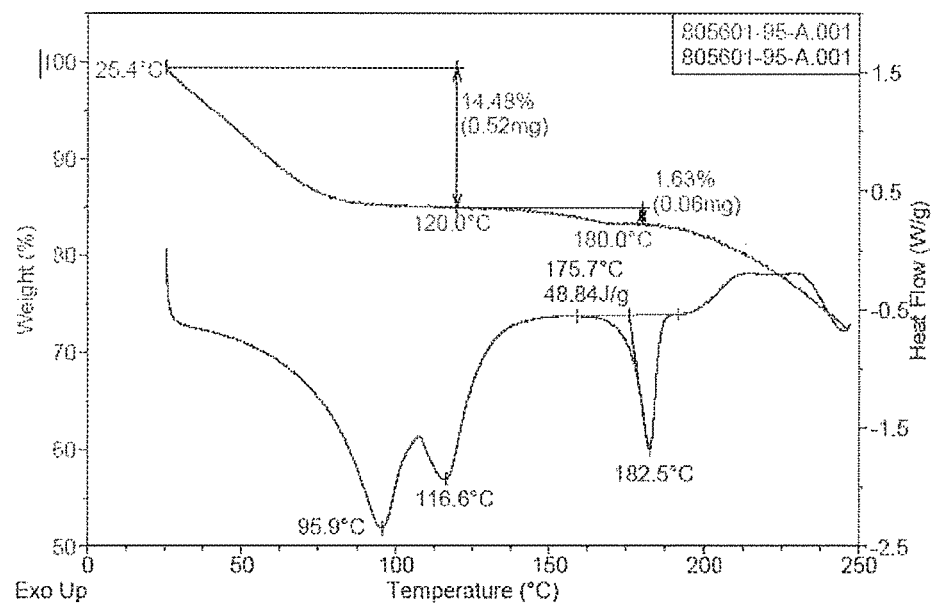
FIG. 8 is TGA and DSC patterns of a polymorph form J of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.

The XRPD pattern of the polymorph form J of (4-((R)-((2S,5R)-4-(3-fluorobenzyl)-(2,5-dimethylpiperazine-1-yl) (3-hydroxyphenyl)methyl)phenyl)(4-methylpiperidine-1-yl) methanone dihydrochloride prepared according to the above method is shown in FIG. 7, and the peak information of the pattern is shown in Table 4. The TGA and DSC patterns of polymorph form J are shown in FIG. 8. As can be seen from FIG. 8, the melting point of the polymorph form J is 182.5° C. (the melting range is 175.7° C. to 182.5° C. as judged by DSC).

TABLE 4

XRPD peak information of polymorph form J

| Position [°2θ] | Height [cts] | Left half-height width [°2θ] | Face distance [Å] | Relative strength [%] |
| --- | --- | --- | --- | --- |
| 8.579 | 148.9 | 0.10 | 10.3 | 20.7 |
| 9.21 | 130.2 | 0.15 | 9.6 | 18.1 |
| 11.40 | 303.0 | 0.13 | 7.8 | 42.1 |
| 11.59 | 242.5 | 0.13 | 7.6 | 33.7 |
| 12.77 | 481.8 | 0.12 | 6.9 | 67.0 |
| 13.17 | 176.6 | 0.10 | 6.7 | 24.6 |
| 13.90 | 133.8 | 0.18 | 6.4 | 18.6 |
| 16.75 | 719.4 | 0.10 | 5.3 | 100.0 |
| 17.14 | 280.4 | 0.13 | 5.2 | 39.0 |
| 19.08 | 158.6 | 0.15 | 4.7 | 22.0 |
| 19.37 | 133.2 | 0.15 | 4.6 | 18.5 |
| 20.54 | 67.6 | 0.20 | 4.3 | 9.4 |
| 21.34 | 112.1 | 0.26 | 4.2 | 15.6 |
| 22.33 | 219.9 | 0.15 | 4.0 | 30.6 |
| 23.28 | 682.9 | 0.15 | 3.8 | 94.9 |
| 23.83 | 83.7 | 0.26 | 3.7 | 11.6 |
| 25.36 | 240.2 | 0.36 | 3.5 | 33.4 |
| 27.23 | 257.3 | 0.18 | 3.3 | 35.8 |
| 27.84 | 126.8 | 0.31 | 3.2 | 17.6 |
| 28.78 | 79.0 | 0.26 | 3.1 | 11.0 |
| 34.13 | 59.4 | 0.41 | 2.6 | 8.3 |

Example 11 Preparation of a Polymorph Form J of (4-((R)-((2S, 5R)-4-(3-fluorobenzyl)-(2,5-dimethylpiperazine-1-yl)(3-hydroxyphenyl)methyl)phenyl)(4-methylpiperidine-1-yl)methanone dihydrochloride The polymorph form B of (4-((R)-((2S,5R)-4-(3-fluorobenzyl)-(2,5-dimethylpiperazine-1-yl)(3-hydroxyphenyl) methyl)phenyl)(4-methylpiperidine-1-yl)methanone dihydrochloride of Example 1 is taken as a starting sample, and placed in an agate mortar, added with very little water or directly ground for 10 min, and the obtained solid is standed at 97.3% relative humidity (RH) and room temperature for 8 days to obtain the polymorph form J.

The XRPD, TGA and DSC patterns of the polymorph form J of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared according to the above method are the same as those of Figures. 7 and 8, respectively.

Example 12 Preparation of a Polymorph Form O of (4-((R)-((2S, 5R)-4-(3-fluorobenzyl)-(2,5-dimethylpiperazine-1-yl)(3-hydroxyphenyl)methyl)phenyl) (4-methylpiperidine-1-yl)methanone dihydrochloride The polymorph form J of (4-((R)-((2S,5R)-4-(3-fluorobenzyl)-(2,5-dimethylpiperazine-1-yl) (3-hydroxyphenyl) methyl)phenyl)(4-methylpiperidine-1-yl)methanone dihydrochloride of Example 10 is taken as a starting sample, heated to 100° C., and naturally cooled to room temperature under the protection of nitrogen to obtain the polymorph form O.

Figure 9:
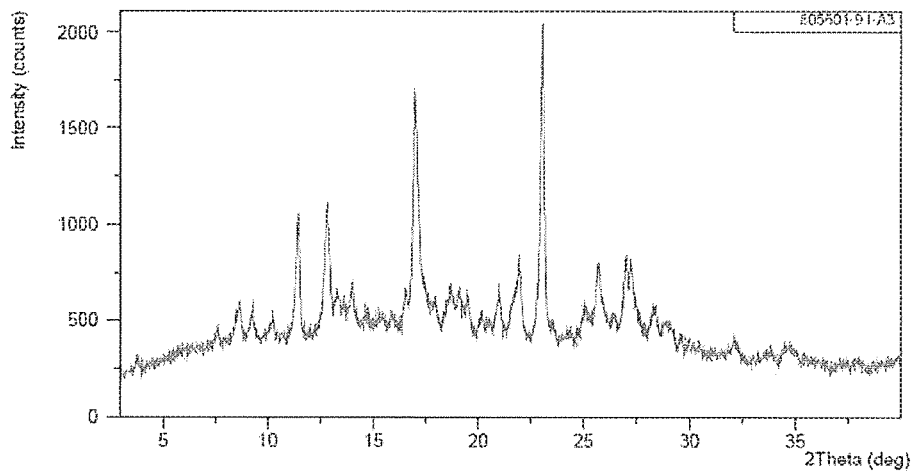
FIG. 9 is an XRPD pattern of a polymorph form O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.
Figure 10:
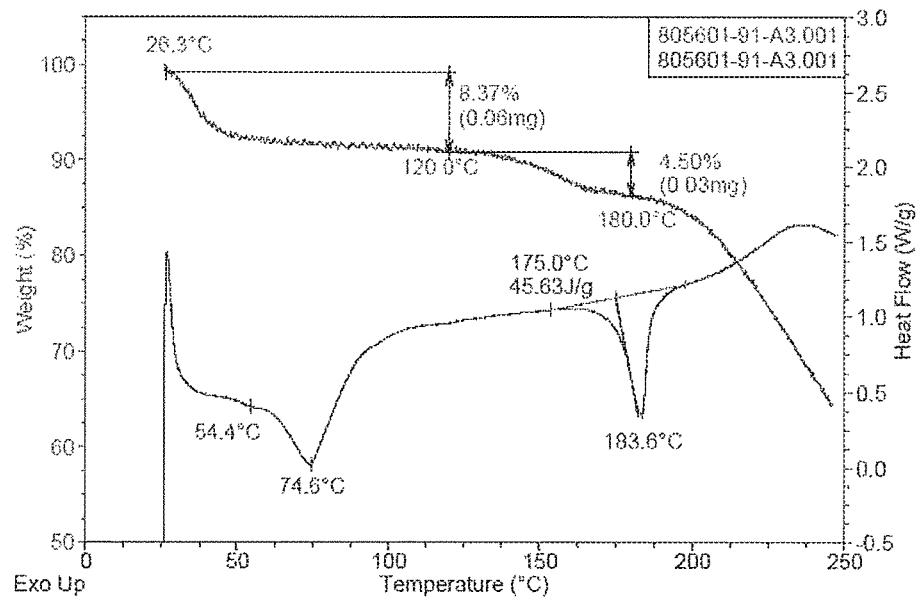
FIG. 10 is TGA and DSC patterns of a polymorph form O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride.

The XRPD pattern of the polymorph form O of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride prepared by the above method is shown in FIG. 9, and the peak information of the diagram is shown in Table 5. The TGA and DSC patterns of the polymorph form O are shown in FIG. 10. As can be seen from FIG. 10, the melting point of the polymorph form O is 183.6° C. (the melting range is 175.0° C. to 183.6° C. as judged by DSC).

TABLE 5

XRPD peak information of polymorph form O.

| Position [°2θ] | Height [cts] | Left half-height width [°2θ] | Face distance [Å] | Relative strength [%] |
|---|---|---|---|---|
| 8.65 | 224.0 | 0.31 | 10.2 | 13.3 |
| 9.27 | 165.3 | 0.31 | 9.5 | 9.8 |
| 11.447 | 685.2 | 0.12 | 7.7 | 40.6 |
| 12.837 | 740.5 | 0.18 | 6.9 | 43.8 |
| 14.01 | 317.6 | 0.15 | 6.3 | 18.8 |
| 17.00 | 1306.4 | 0.13 | 5.2 | 77.3 |
| 18.64 | 277.0 | 0.31 | 4.8 | 16.4 |
| 21.02 | 272.5 | 0.23 | 4.2 | 16.1 |
| 21.97 | 445.5 | 0.18 | 4.0 | 26.4 |
| 23.08 | 1689.5 | 0.13 | 3.9 | 100.0 |
| 25.77 | 403.5 | 0.20 | 3.5 | 23.9 |
| 27.04 | 443.9 | 0.13 | 3.3 | 26.3 |
| 28.35 | 198.5 | 0.31 | 3.1 | 11.8 |
| 29.03 | 116.5 | 0.31 | 3.1 | 6.9 |
| 32.11 | 76.5 | 0.61 | 2.8 | 4.5 |
| 34.58 | 74.6 | 0.51 | 2.6 | 4.4 |

For polymorph forms B, P and F of (4-((R)-((2S,5R)-4-(3-fluorobenzyl)-(2,5-dimethylpiperazine-1-yl)(3-hydroxyphenyl)methyl)phenyl)(4-methylpiperidine-1-yl) dihydrochloride, it should be understood that for those skilled in the art, the solvent used in the preparation process can be replaced according to the actual needs of the experiments.

For example, the solvent used for preparing the polymorph form B may be replaced with a solvent selected from a group consisting of any one or more of acetone, methyl isobutyl ketone, methyl isopropyl ketone, cyclohexane, methylcyclohexane, n-hexane, petroleum ether, ethyl ether, methyl tert-butyl ether, 1,4-dioxane, methyl ethyl ketone, methyl isobutyl ketone, and methyl pyrrolidone, or of any one or more of ethyl acetate, butyl acetate, ethyl formate, isobutyl acetate, isopropyl acetate, methyl acetate, and propyl acetate.

The solvent used for preparing the polymorph form F may be replaced with a solvent selected from a group consisting of any one or more of methanol, ethanol, propanol, ethoxyethanol, 2-methoxyethanol, 1-butanol, 2-butanol, 3-methyl-1-butanol, 2-methyl-1-propanol, 1-pentanol, 1-propanol, 2-propanol, and propylene glycol, or a mixed solvent of any one or more thereof with water.

The solvent used for preparing the polymorph form P may be replaced with a solvent selected from any one or more of acetonitrile, dimethylformamide, diethylacetamide, formamide, dichloromethane, dimethylsulfoxide, and tetrahydrofuran, a mixed solvent of dimethylsulfoxide with water, or a mixed solvent of dimethylformamide with water.

The amount of solvent used can be adjusted according to experimental requirements, and the purpose of the application can be realized. The purpose of the application is not divorced from the design idea of the embodiment of the invention, and is not repeated here, but should be within the protection scope of the application.

Test Example

Rough solubility test, dynamic solubility test, stability test, and relative bioavailability test of a free base of (4-((R)-((2S,5R)-4-(3-fluorobenzyl)-(2,5-dimethylpiperazin-1-yl)(3-hydroxyphenyl)methyl)phenyl) (4-methylpiperidine-1-yl)methanone (hereinafter referred to as the free base) and polymorph forms B, P, F, J and O of its dihydrochloride (hereinafter referred to as polymorph forms B, F, P, J and O, respectively, taken from the samples of Examples 1, 3, 6, 10 and 12) are determined respectively.

Rough Solubility Test 2.0 mg of a free base and 2.0 mg of polymorph forms B, F, P, J and O are respectively taken and placed in 3.0 mL glass bottles. Then the solvent methanol is added step by step, and ultrasound is performed to observe whether the sample is completely dissolved. If the sample is still not completely dissolved after 2.0 mL of solvent is added, the test is stopped to measure the rough solubility of the free base, polymorph forms B, F, P, J and O in methanol respectively.

Using the same method, the rough solubility of the free base, polymorph forms B, P, F, J and O in other organic solvents or water listed in Table 6 are determined respectively. The crude solubility of the free base, polymorph forms B, F, P, J and O are shown in Table 6.

TABLE 6

Rough solubility of free base, polymorph forms B, P, F, J and O

| Solvent | Sample and its solubility (mg/mL) | | | | | |
|---|---|---|---|---|---|---|
| | free base | Polymorph form B | Polymorph form F | Polymorph form P | Polymorph form J | Polymorph form O |
| Methanol | 22.0-23.0 | 24.0-48.0 | 22.0-42.0 | 24.0-36.0 | 26.0-52.0 | 23.0-49.0 |
| Ethanol | 5.2-5.6 | 14.7-22.0 | 13.5-21.5 | 12.3-19.0 | 14.8-23.0 | 13.6-22.0 |
| Isopropyl alcohol | 4.6-4.9 | 14.0-21.0 | 13.0-20.5 | 11.2-20.0 | 15.2-23.5 | 12.3-21.5 |
| Acetonitrile | 42.9-43.1 | 12.8-13.1 | 12.2-13.5 | 11.8-12.3 | 13.2-14.4 | 12.1-13.0 |
| Acetone | 29.0-30.8 | <1.4 | <1.2 | <1.0 | <1.4 | <1.2 |
| Methyl isobutyl ketone | 3.5-3.8 | <1.0 | <1.2 | <1.2 | <1.0 | <1.0 |
| Ethyl acetate | 7.7-9.0 | <1.2 | <1.2 | <1.2 | <1.4 | <1.2 |
| Isopropyl acetate | 3.3-3.5 | <1.0 | <1.1 | <1.0 | <1.2 | <1.1 |
| Methyl tert-butyl ether | 2.4-2.6 | <1.4 | <1.2 | <1.0 | <1.2 | <1.4 |
| Tetrahydrofuran | 17.0-22.6 | <1.6 | <1.4 | <1.2 | <1.6 | <1.4 |
| 2-methyltetrahydrofuran | 4.7-5.1 | <1.1 | <1.0 | <1.0 | <1.2 | <1.1 |
| 1,4-dioxane | 12.0-15.0 | 1.6-1.7 | 1.5-1.7 | 1.7-2.0 | 1.8-2.3 | 1.5-1.8 |

TABLE 6-continued

Rough solubility of free base, polymorph forms B, P, F, J and O

| Solvent | Sample and its solubility (mg/mL) | | | | | |
|---|---|---|---|---|---|---|
| | free base | Polymorph form B | Polymorph form F | Polymorph form P | Polymorph form J | Polymorph form O |
| N-methylpyrrolidone | 7.4-8.7 | 21.0-42.0 | 21.5-40.0 | 22.0-40.0 | 25.0-46.0 | 21.8-40.6 |
| dimethyl sulfoxide | 9.3-11.2 | >44.0 | >42.5 | >42.0 | >48.0 | >43.0 |
| dichloromethane | 10.0-12.5 | 1.7-1.8 | 1.4-1.6 | 1.5-1.6 | 1.8-2.0 | 1.4-1.5 |
| Toluene | 1.3-1.4 | <1.1 | <1.1 | <1.0 | <1.2 | <1.1 |
| N-heptane | <1.5 | <1.2 | <1.1 | <1.0 | <1.4 | <1.2 |
| N,N-dimethylacetamide | 11.5-15.3 | >52.0 | >51.0 | >50.0 | >53.0 | >52.0 |
| Water | <1.1 | 6.4-7.2 | 5.8-6.7 | 6.0-6.8 | 6.0-7.4 | 6.2-7.2 |
| Chloroform | 20.7-31.0 | 27.0-54.0 | 26.5-53.0 | 25.0-52.0 | 28.0-56.0 | 25.8-52.8 |
| 2-MeTHF | 4.7-5.1 | <1.1 | <1.1 | <1.0 | <1.3 | <1.1 |

Dynamic Solubility Test

The dynamic solubility of a free base, polymorph forms B, P, F, J and O in water or a biological medium such as Stimulated Gastric Fluid (SGF), Fed State Simulated Intestinal Fluid (FeSSIF) or Fasted State Simulated Intestinal Fluid (FaSSIF) is determined.

Formulation of Stimulated Gastric Fluid (SGF)

0.2 g sodium chloride and 0.1 g Triton X-100 is weighed and placed into a 100 mL volumetric flask. Purified water is added to dissolve. A stir is performed until the solid is completely dissolved. About 135 μL concentrated hydrochloric acid solution (37%, 12 mmoL/L) is added, then the pH is adjusted to 1.8 with 1 mmoL/L hydrochloric acid or 1 mmoL/L sodium hydroxide. Finally, the volume is fixed with purified water to obtain Stimulated Gastric Fluid (SGF) for later use.

Formulation of Fed State Simulated Intestinal Fluid (FeSSIF)

Each of 0.41 mL glacial acetic acid, 0.20 g sodium hydroxide and 0.59 g sodium chloride is weighed and placed to a 50 mL volumetric flask. About 48 mL purified water is added to dissolve, the pH is adjusted to 5.0 with 1 mmoL/L hydrochloric acid or 1 mmoL/L sodium hydroxide, and the volume is fixed with purified water. Then 0.56 g of Simulated Intestinal Fluid powder (SIF powder for short, which is composed of soybean lecithin and sodium taurocholate with a molar ratio of 4:1) is added, stirred and ultrasonically dissolved to obtain Fed State Simulated Intestinal Fluid (FeSSIF) for later use.

Formulation of Fasted State Simulated Intestinal Fluid (FaSSIF)

Each of 0.17 g of anhydrous sodium dihydrogen phosphate ($NaH_2PO_4$), 0.021 g of sodium hydroxide and 0.31 g of sodium chloride is weighed and placed into a 50 mL volumetric flask. About 48 mL of purified water is added to dissolve, the pH is adjusted to 6.5 with 1 mmoL/L hydrochloric acid or 1 mmoL/L sodium hydroxide, and the volume is fixed with purified water. 0.11 g of SIF powder is added, stirred and ultrasonically dissolved to obtain Fasted State Simulated Intestinal Fluid (FaSSIF) for later use.

Each 30 mg of the free base, and polymorph forms B, P, F, J and O are weighed. 3 mL of purified water, Stimulated Gastric Fluid (SGF), Fed State Simulated Intestinal Fluid (FeSSIF) or Fasted State Simulated Intestinal Fluid (FaSSIF)) is added and oscillated at room temperature. 0.6 mL of suspension is taken each time at a set time point, filtered and separated with a 0.45 μm nylon filter membrane, then XRPD characterization is performed on the solid sample, and the concentration in the clear solution is measured by HPLC. Table 7 shows the dynamic solubility of the free base, polymorph forms B, P, F, J, and O, the pH in the clear solution, and the crystal forms of insoluble solid samples characterized by XRPD.

TABLE 7

Dynamic Solubility of Free Base, Polymorph forms B, P, F, J and O, pH in Clear Solution and Crystal Forms of Insoluble Solid Samples

| medium | Time | Free base | | | Polymorph form p | | | Polymorph form F | | |
|---|---|---|---|---|---|---|---|---|---|---|
| | | Solubility (mg/ml) | pH | Crystal form | Solubility (mg/ml) | pH | Crystal form | Solubility (mg/ml) | pH | Crystal form |
| Water | 1 | <LOQ | 5.6 | invariability | 6.0 | 1.9 | invariability | 5.8 | 1.8 | invariability |
| | 2 | <LOQ | 5.7 | invariability | 6.1 | 1.9 | invariability | 5.9 | 1.9 | invariability |
| | 4 | <LOQ | 5.6 | invariability | 6.0 | 1.9 | invariability | 5.8 | 1.8 | invariability |
| | 24 | <LOQ | 5.8 | invariability | 0.088 | 1.6 | Monohydrochloride | 0.16 | 1.5 | Monohydrochloride |
| SGF | 1 | 2.1 | 1.9 | invariability | 3.4 | 1.6 | invariability | 3.0 | 1.6 | invariability |
| | 2 | 2.7 | 1.9 | invariability | 3.4 | 1.7 | invariability | 3.4 | 1.6 | invariability |
| | 4 | 2.7 | 1.9 | invariability | 3.0 | 1.6 | invariability | 3.4 | 1.6 | invariability |
| | 24 | 3.2 | 2.1 | invariability | 3.7 | 1.5 | invariability | 3.2 | 1.4 | invariability |
| FeSSIF | 1 | 0.059 | 4.9 | invariability | 0.43 | 5.0 | invariability | 0.42 | 4.8 | invariability |
| | 2 | 0.063 | 5.0 | invariability | 0.45 | 4.9 | invariability | 0.43 | 4.9 | invariability |
| | 4 | 0.062 | 5.0 | invariability | 0.47 | 5.0 | invariability | 0.43 | 4.9 | invariability |
| | 24 | 0.081 | 5.0 | invariability | 0.44 | 4.6 | invariability | 0.44 | 4.9 | invariability |
| FaSSIF | 1 | 0.013 | 6.5 | invariability | 0.49 | 3.0 | invariability | 0.33 | 3.5 | invariability |
| | 2 | 0.017 | 6.5 | invariability | 0.51 | 2.7 | invariability | 0.30 | 4.6 | invariability |
| | 4 | 0.016 | 6.5 | invariability | 0.71 | 2.2 | invariability | 0.46 | 4.2 | invariability |
| | 24 | 0.027 | 6.5 | invariability | 0.41 | 2.6 | invariability | 0.51 | 4.5 | invariability |

TABLE 7-continued

Dynamic Solubility of Free Base, Polymorph forms B, P, F, J and O, pH in Clear Solution and Crystal Forms of Insoluble Solid Samples

| medium | Time | Polymorph form O | | Polymorph form B | | Polymorph form J | |
|---|---|---|---|---|---|---|---|
| | | Solubility (mg/ml) | Crystal pH form | Solubility (mg/ml) | Crystal pH form | Solubility (mg/ml) | Crystal pH form |
| Water | 1 | 6.2 | 1.9 invariability | 6.4 | 1.8 amorphism | 6.0 | 1.8 amorphism |
| | 2 | 6.4 | 1.8 invariability | 6.6 | 1.8 amorphism | 6.2 | 1.7 amorphism |
| | 4 | 6.4 | 1.9 invariability | 6.8 | 1.8 amorphism | 6.2 | 1.7 amorphism |
| | 24 | 0.24 | 1.4 Monohydrochloride | 0.12 | 1.7 Monohydrochloride | 0.067 | 1.4 Monohydrochloride |
| SGF | 1 | 3.0 | 1.5 invariability | 3.6 | 1.5 amorphism | 3.2 | 1.7 amorphism |
| | 2 | 3.2 | 1.6 invariability | 3.6 | 1.5 amorphism | 3.4 | 1.5 amorphism |
| | 4 | 3.2 | 1.6 invariability | 3.4 | 1.5 amorphism | 3.4 | 1.5 amorphism |
| | 24 | 3.5 | 1.7 invariability | 3.3 | 1.5 amorphism | 3.3 | 1.6 amorphism |
| FeSSIF | 1 | 0.38 | 5.0 invariability | 0.42 | 4.8 amorphism | 0.45 | 4.8 amorphism |
| | 2 | 0.38 | 4.8 invariability | 0.45 | 4.8 amorphism | 0.45 | 5.0 amorphism |
| | 4 | 0.42 | 5.0 invariability | 0.43 | 4.8 amorphism | 0.43 | 4.9 amorphism |
| | 24 | 0.40 | 5.2 invariability | 0.44 | 4.6 amorphism | 0.46 | 4.7 amorphism |
| FaSSIF | 1 | 0.35 | 2.2 invariability | 0.22 | 2.5 amorphism | 0.36 | 2.8 amorphism |
| | 2 | 0.37 | 2.0 invariability | 0.33 | 2.6 amorphism | 0.42 | 3.0 amorphism |
| | 4 | 0.42 | 2.4 invariability | 0.54 | 2.5 amorphism | 0.38 | 2.8 amorphism |
| | 24 | 0.38 | 2.2 invariability | 0.80 | 2.3 amorphism | 0.38 | 2.6 amorphism |

After testing, it can be concluded from Table 7 that compared with the free base, the solubility of salt-forming hydrochloride polymorph forms P, F, O, B and J in water, Fed State Simulated Intestinal Fluid (FeSSIF) and Fasted State Simulated Intestinal Fluid (FaSSIF) is significantly improved, and the solubility in Stimulated Gastric Fluid (SGF) is close to or slightly improved with the free base.

Stability Test

Both polymorph forms B and O will change into amorphous under dynamic moisture adsorption. Therefore, only the physical stability of polymorph forms P, F and J under different environments will be examined below.

The physical stability of polymorph forms P, F and J are studied under the following four different environmental conditions.

Figure 11:
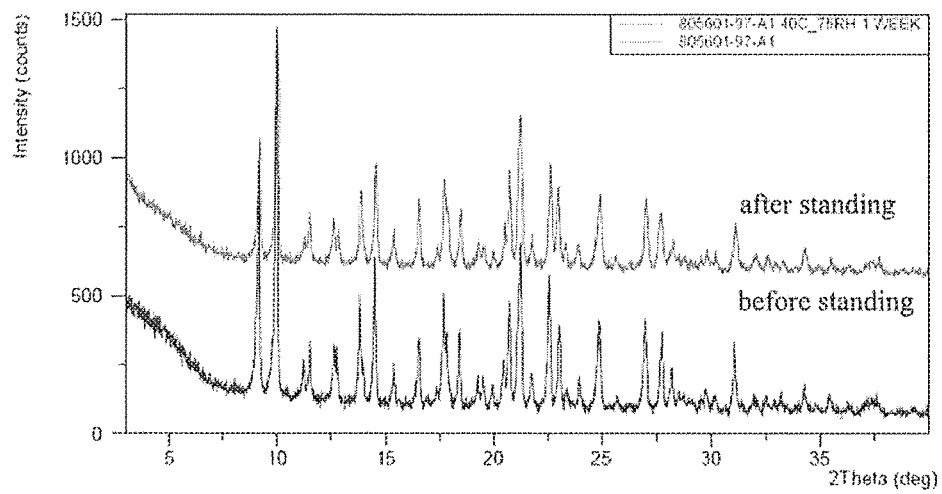
FIGS. 11 to 13 are XRPD comparative patterns of polymorph forms P, F and J before and after one week of storage at 40° C. and 75% RH, respectively.
Figure 12:
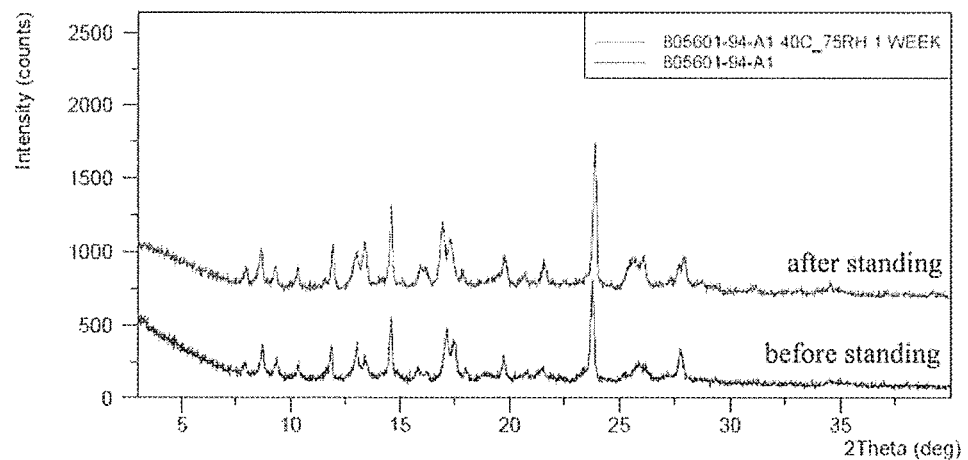
Figure 13:
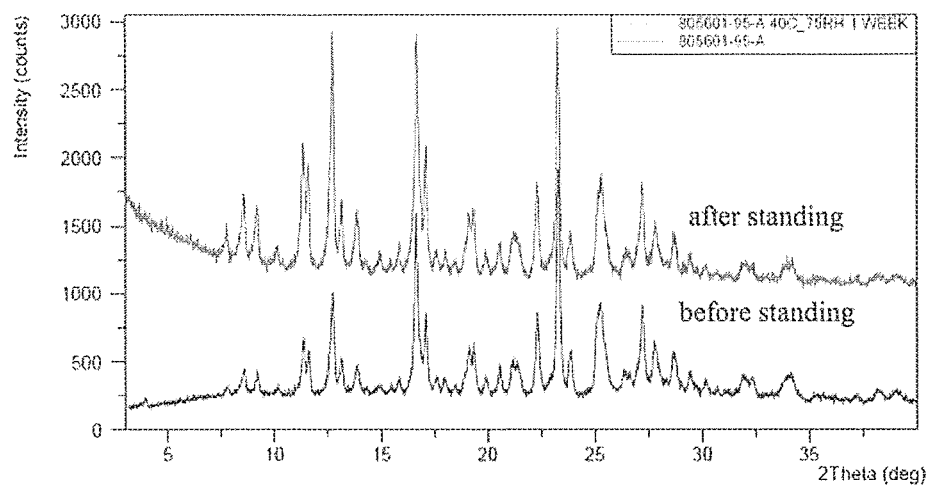

Condition 1: 40° C./75% RH/Week 10 mg to 15 mg of polymorph forms P, F and J are each weighed and placed in a 1.5 mL glass bottle, and the glass bottle is placed open for one week in a constant temperature and humidity box under the conditions of 40° C. and 75% RH, and then XRPD tests are carried out on the polymorph forms P, F and J to determine whether the crystal forms of the samples change. FIGS. 11 to 13 are XRPD comparative patterns of polymorph forms P, F and J before and after one week of storage at 40° C. and 75% RH, respectively.

Condition 2: Dry Overnight at 60° C.

Figure 14:
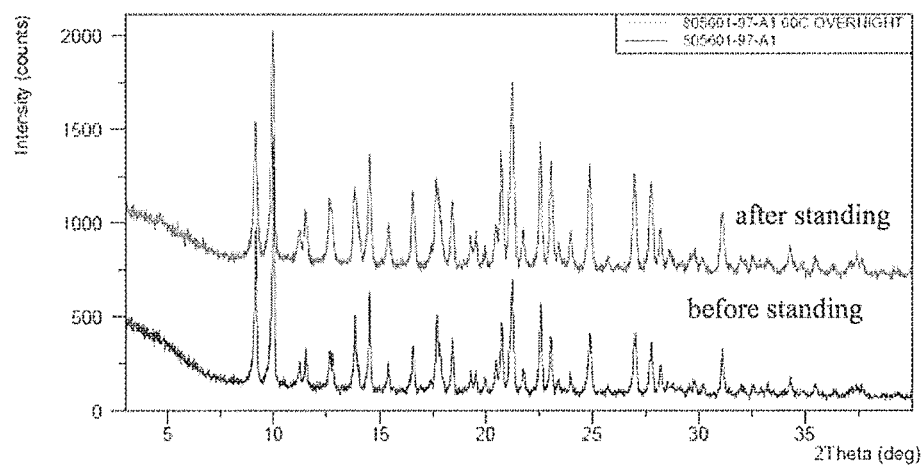
FIGS. 14 to 16 are XRPD comparative patterns of polymorph forms P, F and J before and after standing overnight under a drying condition of 60° C.
Figure 15:
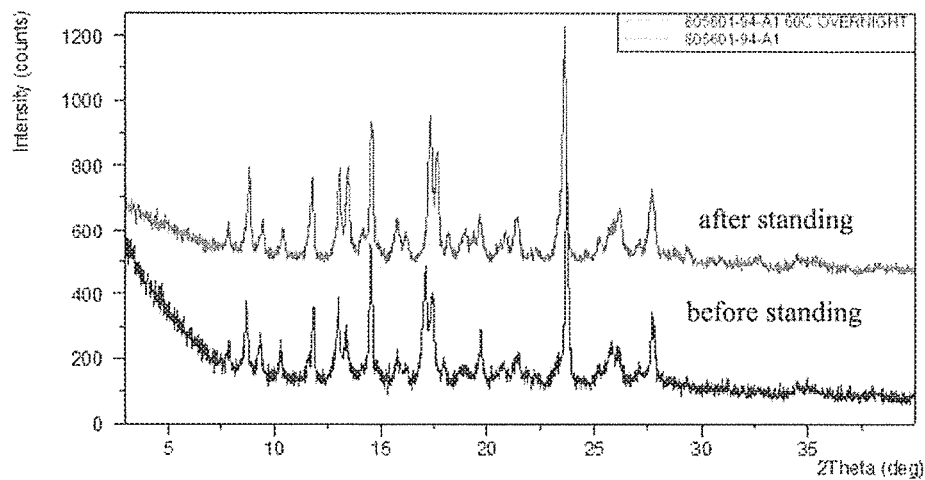
Figure 16:
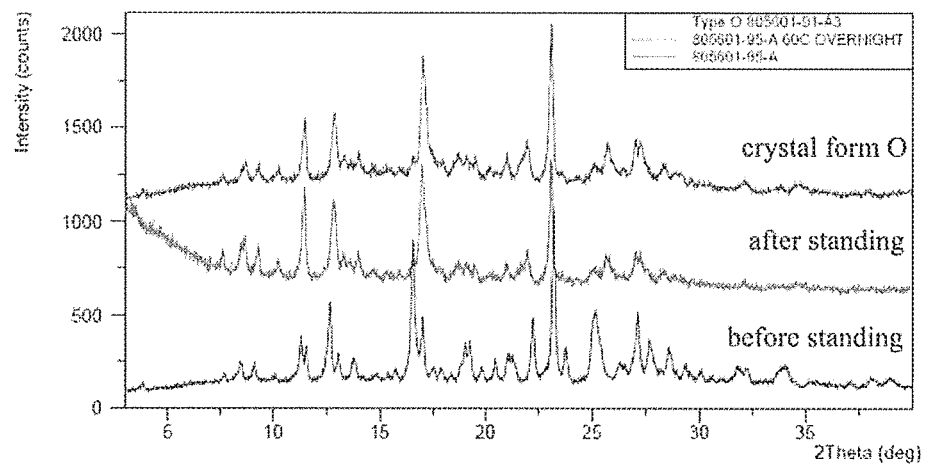

10 mg to 15 mg of polymorph forms P, F and J are each weighed and placed in a 1.5 mL glass bottle, and the glass bottle is placed open overnight in a constant temperature drying oven under the condition of 60° C. Then XRPD test is carried out on the polymorph forms P, F and J to determine whether the crystal forms of the samples change. FIGS. 14 to 16 are XRPD comparative patterns of the polymorph forms P, F and J before and after being placed overnight under a drying condition of 60° C., respectively.

Figure 17:
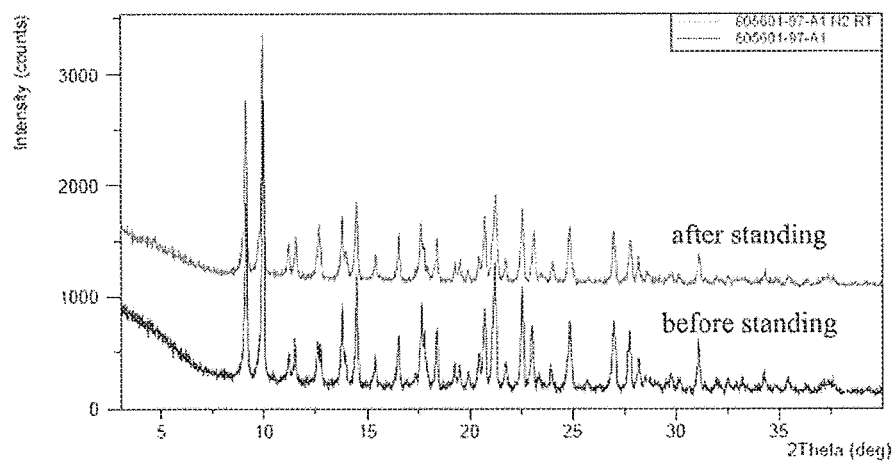
FIGS. 17 to 19 are XRPD comparative patterns of polymorph forms P, F and J before and after nitrogen purging for 2 h at 60° C., respectively.
Figure 18:
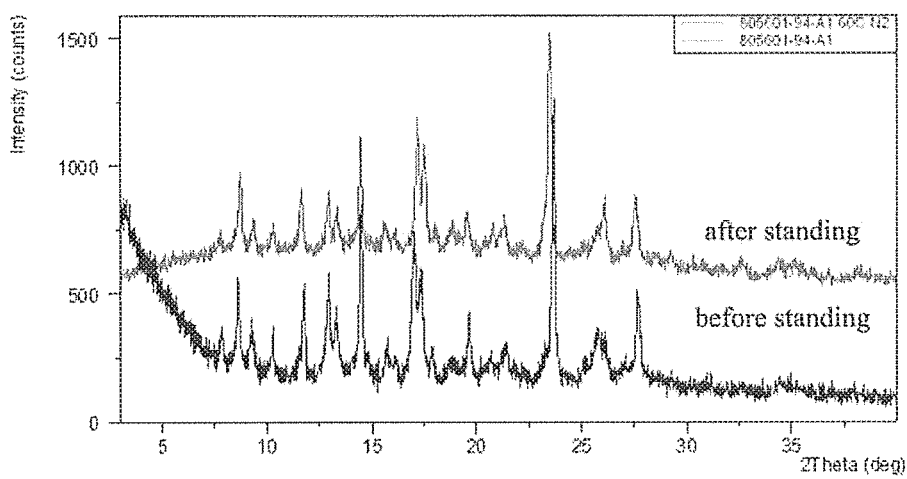
Figure 19:
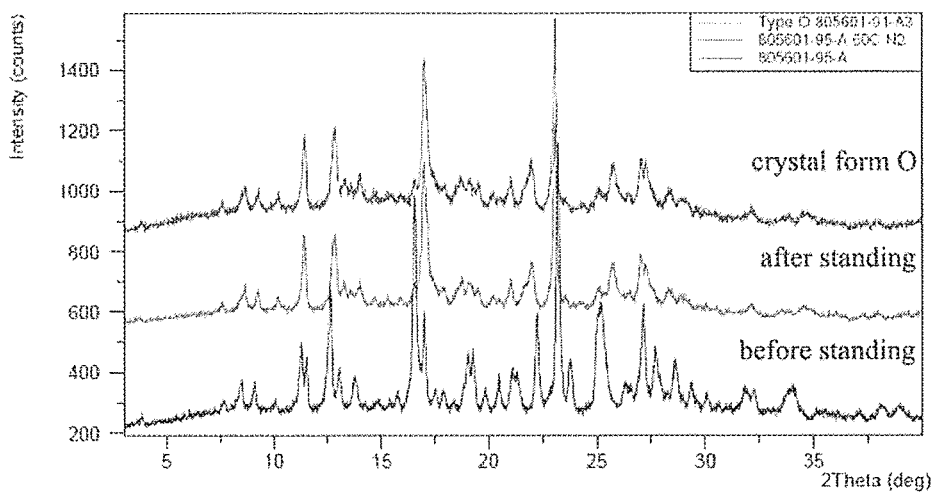

Condition 3: Nitrogen Purging at 60° C. for 2 h 10 mg to 15 mg of polymorph forms P, F and J are each weighed and placed in a 1.5 mL glass bottle, and nitrogen is purged for 2 h under the condition of 60° C. in a nitrogen blower, and then XRPD tests are carried out on the polymorph forms P, F and J to determine whether the crystal forms of the samples change. FIGS. 17 to 19 are XRPD comparative patterns of the polymorph forms P, F and J before and after nitrogen purging for 2 h at 60° C., respectively.

Figure 20:
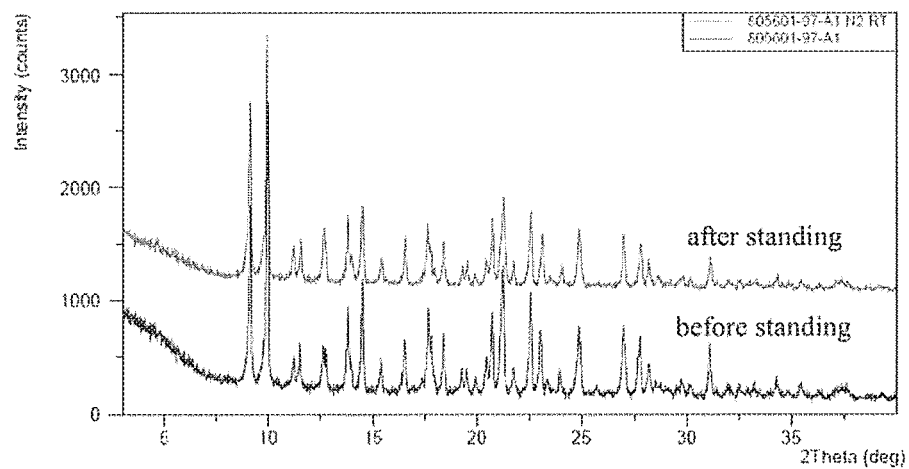
FIGS. 20 to 22 are XRPD comparative patterns of polymorph forms P, F and J before and after nitrogen purging overnight at room temperature, respectively.
Figure 21:
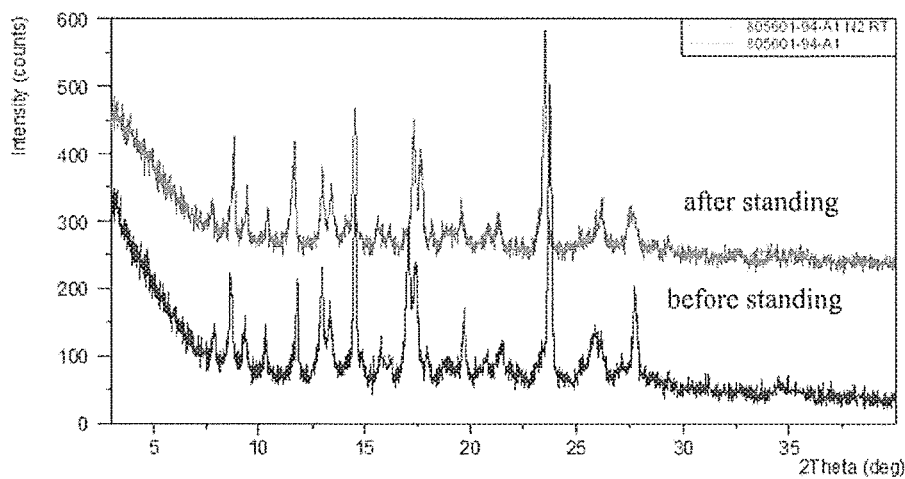
Figure 22:
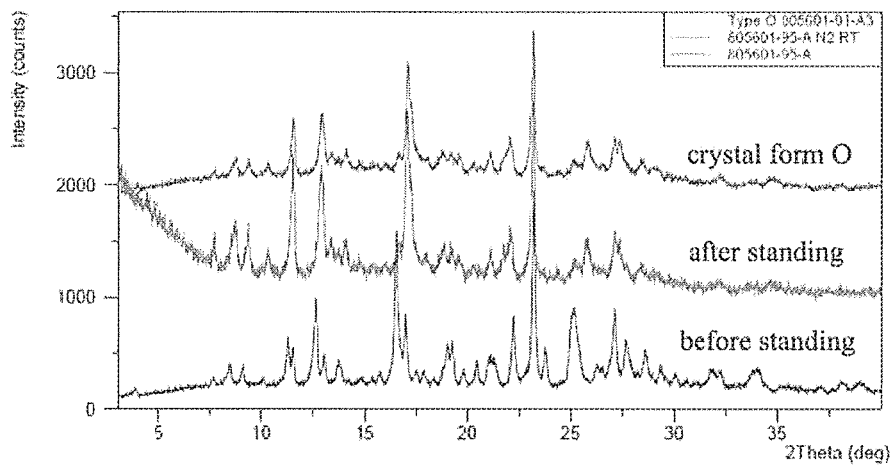

Condition 4: Room Temperature Nitrogen Blowing Overnight 10 mg to 15 mg of polymorph forms P, F and J are each weighed and placed in a 3 mL glass bottle, nitrogen is blown overnight at room temperature in a nitrogen blower, and then XRPD tests are carried out on the polymorph forms P, F and J to determine whether the crystal forms of the samples change. FIGS. 20 to 22 are XRPD comparative patterns of the polymorph forms P, F and J before and after nitrogen purging overnight at room temperature, respectively.

Judging from XRPD comparative patterns of various polymorph forms, the physical stability properties of the polymorph forms P, F and J are obtained, and the results are shown in Table 8.

TABLE 8

Physical Stability Properties of Polymorph forms P, F and J

| Polymorph forms | Crystal form, after 40° C./ 75% RH for one week | Crystal form, after drying at 60° C. overnight | Crystal form, after nitrogen purging at 60° C. for 2 h | Crystal form, after nitrogen purging overnight at room |
|---|---|---|---|---|
| Polymorph form P | invariability | invariability | invariability | invariability |
| Polymorph form F | invariability | invariability | invariability | invariability |
| Polymorph form J | invariability | Polymorph form O | Polymorph form O | Polymorph form O |

For polymorph forms P and F, the crystal forms remain unchanged after standing under the four conditions, and the polymorph forms P and F have good stability. For a polymorph form F, the characteristic peak after standing under condition 1 is slightly offset from the characteristic peak before standing, but the crystal form after standing still belongs to the polymorph form F.

For a polymorph form J, the crystal form does not change after standing for one week at 40° C./75% RH, and is converted into a polymorph form O under the other three conditions.

Relative Bioavailability Test

HPLC-MS/MS method is used to detect the blood drug concentration of target drugs in SPF-grade SD rats, and the relative bioavailability of 0.5% CMC-Na suspension of a free base and 0.5% CMC-Na solution of a polymorph form P are calculated and compared.

Formulation of 0.5% CMC-Na Suspension of a Target Drug in a Free Base Group:

60.46 mg of a free base is accurately weighed and placed into a 15 mL centrifuge tube, 12 mL of 0.5% CMC-Na solution is measured and added into the centrifuge tube with a measuring cylinder, vortexed for 5 min, and ultrasonically dispersed for 15 min to obtain 0.5% CMC-Na suspension of free base with a concentration of 5.04 mg/ml, which is currently formulated when using and vibrated at any time during administration.

Formulation of 0.5% CMC-Na Solution of a Target Drug of a Polymorph Form P Group:

60.05 mg of a polymorph form P is accurately weighed and placed into a 15 mL centrifuge tube, 12 mL of 0.5% CMC-Na solution is measured and added into the centrifuge tube with a measuring cylinder, vortexed for 5 min, and ultrasonically dispersed for 15 min to obtain 0.5% CMC-Na solution of 5.00 mg/mL polymorph form P, which is currently formulated when using.

Twelve SPF-grade SD rats are selected and randomly divided into a free base group and a polymorph form P group with 6 rats in each group (both male and female). Animals are fasted for 12 h but have free access to water. Weighing is performed and, the administration volume of each rat is calculated according to the animal weight, so that the administration dose is 20 mg/kg·bw. During administration, the drugs are each administrated by gavage, and 0.5% CMC-Na suspension/solution of the above two target drugs are extracted by 2 mL syringe respectively. The gavage needle is inserted into the stomach from the corner of the rat's mouth and pushed the solution thereto.

Figure 23:
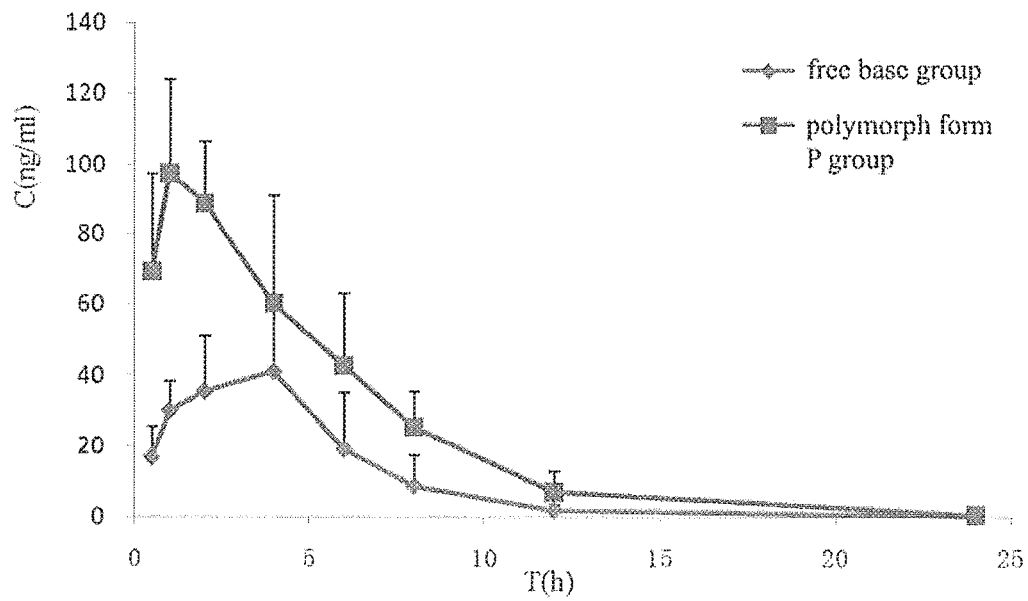
FIG. 23 is a blood drug concentration pattern of target drugs in a free base group and polymorph form P group with time variation in rat plasma.

Blood is collected from the fundus venous plexus of rats at 0.2 mL before (0 h) and 0.5, 1, 2, 4, 6, 8, 12 and 24 h after administration, anticoagulated with 300 IU/mL heparin (1:20) and centrifuged (3000 r/min) for 15 min. After plasma separation, the blood drug concentration of the target drug is determined by HPLC-MS/MS. The obtained blood drug concentration-time curve is shown in FIG. 23. The main pharmacokinetic parameters of the two groups calculated by DAS2.0 software are shown in Table 9.

TABLE 9

Average Pharmacokinetic Parameters of Free Base Group and Polymorph form P Group ($\bar{x} \pm s$, n = 6)

| Group | $t_{1/2z}$ (h) | Tmax (h) | Cmax (ng/mL) | $AUC_{(0-24h)}$ (ng/mL * h) |
|---|---|---|---|---|
| Free base group | 2.4 ± 0.8 | 3.6 ± 0.9 | 51.68 ± 6.56 | 288.6 ± 64.7 |
| Polymorph form P group | 2.5 ± 0.8 | 1.3 ± 0.5 | 98.12 ± 25.25 | 583.5 ± 73.6 |

The average $AUC_{(0-24h)A}$ in the free base group is 288.6 ng/mL * h, and the average $AUC_{(0-24h)P}$ in the polymorph form P group is 583.5 ng/mL * h. The relative bioavailability (F) is calculated as follows:

$$F = \frac{AUC_{(0-24h)P}}{AUC_{(0-24h)A}} \times 100\% = 583.5/288.6 \times 100\% = 202\%$$

In other words, under the present experimental conditions, the bioavailability of the polymorph form P is 202% for the free base. According to the pharmacokinetic parameters, the polymorph form P aqueous solution reaches the peak faster and the average peak concentration is higher.

Referring to the above-mentioned bioavailability test of the polymorph form P, the bioavailability tests of polymorph forms F, O, B and J are conducted respectively. Different from the bioavailability test of the polymorph form P, rats are given 0.5% CMC-Na solution of the polymorph form F, O, B or J by gavage respectively. Other operations are the same as the above bioavailability test. The obtained results are consistent with the results of 0.5% CMC-Na solution of the polymorph form P, and the polymorph forms F, O, B and J have better bioavailability than free base.

The polymorph forms P, F, O, B and J have higher dynamic solubility than the free base, and are easier to penetrate cell membrane and be absorbed when entering animal body, thus having higher bioavailability.

Application Example: Forced Swimming Test

Forced swimming test is used to test the antidepressant effects of polymorph forms P, F, O, B and J.

(1) Specific Test Environment:

the swimming test equipment is a transparent glass round cylinder with a height of 46 cm and an inner diameter of 20 cm, the test water temperature is 23° C.~25° C., the test water depth is 30 cm, and each cylinder is used only once.

(2) Formulation of Specific Reagents

Vehicle control solution: 0.9% normal saline.

Formulation of Experimental Reagents for Experiment Group 1:

300 mg of a polymorph form P is weighed with an electronic balance, and the polymorph form P is dissolved with 0.9% normal saline, and finally the volume is fixed to 100 mL with 0.9% normal saline, at this time, the concentration of dihydrochloride in the experimental reagent is 3 mg/mL for later use.

Formulation of Experimental Reagents for Experiment Group 2:

600 mg of a polymorph form P is weighed with an electronic balance, and the polymorph form P is dissolved with 0.9% normal saline, and finally the volume is fixed to 100 mL with 0.9% normal saline, at this time, the concentration of dihydrochloride in the experimental reagent is 6 mg/mL for later use.

Formulation of Positive Control Solution:

400 mg of desipramine (DMI) is weighed with an electronic balance, DMI is dissolved with 0.9% normal saline, and then the volume is fixed to 100 mL with 0.9% normal saline for later use.

(3) Test Methods

Forty SPF-grade SD rats are prepared and randomly divided into 4 groups, namely vehicle control group, positive control group, experimental group 1 and experimental group 2, with 10 rats in each group. The day before the test, the rats were placed in water for 15 min to pre-swim for 15 min in advance to adapt to the swimming test environment, then taken out and dried, placed in the cage under an infrared lamp for 15 min and then placed in the original cage. After 24 h, a formal swimming test is conducted, that is, the rats are put into water again after 24 h, and the rats are continuously observed for 5 min. The swimming process are needed to be photographed. The drug is administered during two swimming sessions.

(4) Administration Capacity and Dosage, Route and Cycle

Administrations are carried out according to the administration capacity and route shown in Table 10.

TABLE 10

Capacity (Dosage) and Route of Administration for Each Group

| Group | Administration capacity | Administration dosage | Administration route |
|---|---|---|---|
| Vehicle control group | 10 mL/kg | 10 mL/kg | Subcutaneous administration (Sc) |
| Positive control group | 10 mL/kg | 40 mg/kg | Intraperitoneal administration (Ip) |
| Experiment group 1 | 10 mL/kg | mg/kg | Subcutaneous administration (Sc) |
| Experiment group 2 | 10 mL/kg | 60 mg/kg | Subcutaneous administration (Sc) |

2) Swimming—if the rats have obvious swimming behaviors, not only to keep their heads above the water surface, or to travel around in a round cylinder, they are evaluated as swimming;

3) Wall climbing—the rats' front paws have obvious behavior of entering and leaving the water surface, usually, rats are evaluated as wall climbing in front of the round cylinder wall.

All behavioral are scored by a single person. To avoid bias of observation, the scorer only observed and scored without knowing the administration situations. Then multiple test fragments are randomly selected, and the scorer will score the second round to determine the accuracy of observation. The test video is scored again by the second scorer to determine the accuracy between scorers. The second scorer are also required to observe without knowing the drug administration. Finally, in order to determine the effectiveness of the method, the first scorer scored again and recorded the duration of various behaviors with a stopwatch.

(6) Statistical Methods

SPSSwin11.0 software is used for variance analysis. One-way variance analysis is used for homogeneity of variance, and Dunnett test is used for heterogeneity of variance.

(7) Test Results

According to the above behavior score recording results and statistical methods, the following test results are obtained.

TABLE 11

Number of Static, Swimming and Wall climbing Behavior ($\bar{x} \pm$ SEM) of Rats in Each Group

| Group | Number of case (only) | Number of behaviors (times) | | |
|---|---|---|---|---|
| | | Static | Swimming | Wall climbing |
| vehicle control group | 10 | 29.8 ± 2.6 | 17.3 ± 2.1 | 12.9 ± 1.7 |
| Positive control group | 10 | 7.5 ± 1.3▲▲▲ | 28.6 ± 3.1▲▲ | 23.9 ± 2.4▲▲ |
| Experiment group 1 | 10 | 9.1 ± 1.5▲▲▲ | 28.5 ± 4.3▲ | 22.8 ± 3.8▲ |
| Experiment group 2 | 10 | 17.7 ± 1.6▲▲▲ | 24.4 ± 2.8▲ | 18.2 ± 1.1▲ |

Note:
compared with vehicle control group:
▲$p < 0.05$,
▲$p < 0.01$,
▲$p < 0.001$.

The positive control group containing DMI is administered three times, at 23.5 h, 5 h and 1 h before the formal swimming test respectively. Vehicle control group, experimental group 1 and experimental group 2 are each administered only once and subcutaneously within 1 h.

(5) Behavior Score

The behaviors of the rats are scored by the scorer every 5 seconds after recording the experiment.

Figure 24:
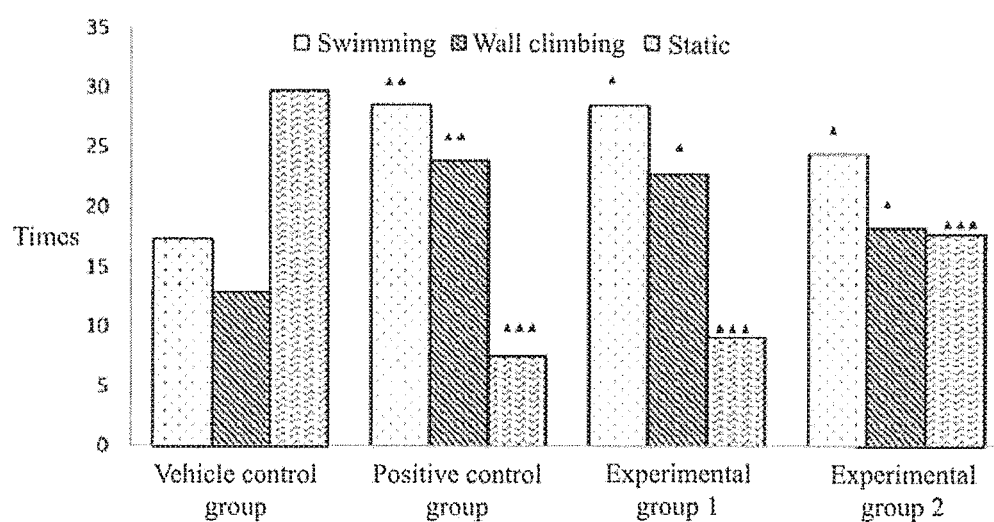
FIG. 24 is a statistical chart showing the times of static, swimming and climbing behaviors of each group of rats in the forced swimming experiment.

Record the following three behaviors:

1) Static—when the rat floats on the water surface without struggling and moves only to keep its head above the water surface, the rat is evaluated as static;

The results shown in Table 11 and FIG. 24 show that: for the positive control group where the positive control solution containing 40 mg/kg desipramine (DMI) is administered to the rats, the static times of the rats can be reduced, the swimming times of the rats can be increased, and the wall climbing times can be increased. Compared with the vehicle control group, there is a significant difference ($P<0.001$, $P<0.01$, $P<0.01$), indicating that the test method is feasible. For the experimental group 1 and the experimental group 2 where respectively experimental reagents containing a polymorph form P of 30 mg/kg and 60 mg/kg are administered to the rats, the static times of forced swimming of the rats can be obviously reduced, the swimming times of the rats can be increased, and the wall climbing times can be increased. Compared with the vehicle control group, there is a significant difference (P<0.001, P<0.05, P<0.05).

TABLE 12

Duration of Static, Swimming and Wall climbing Behavior ($\bar{x}$ ± SEM) of Rats in Each Group

| Group | Number of cases (only) | Behavior duration (seconds) | | |
|---|---|---|---|---|
| | | Static | Swimming | Wall climbing |
| Vehicle control group | 10 | 149.0 ± 13.0 | 86.5 ± 10.5 | 64.5 ± 8.5 |
| Positive control group | 10 | 37.5 ± 6.5▲▲▲ | 143.0 ± 15.5▲▲ | 119.5 ± 12.0▲▲ |
| Experiment group 1 | 10 | 45.5 ± 7.5▲▲▲ | 142.5 ± 21.5▲ | 114.0 ± 19.0▲ |
| Experiment group 2 | 10 | 88.5 ± 8.0▲▲▲ | 122.0 ± 14.0▲ | 91.0 ± 5.5▲ |

Note:
compared with vehicle control group:
▲$p < 0.05$,
▲▲$p < 0.01$,
▲▲▲$p < 0.001$.

The results in Table 12 show that: for the positive control group where the positive control solution containing 40 mg/kg desipramine (DMI) is administered to the rats, the static duration of rats can be reduced, the swimming duration of the rats can be increased, and the wall climbing duration can be increased. Compared with the vehicle control group, there is a significant difference (P<0.001, P<0.01, P<0.01), indicating that the test method is feasible. For the experimental group 1 and the experimental group 2 where respectively experimental reagents containing a polymorph form P of 30 mg/kg and 60 mg/kg are administered to the rats, the static duration of forced swimming of the rats can be obviously reduced, the swimming duration of the rats can be increased, and the wall climbing duration can be increased. Compared with the vehicle control group, there is a significant difference (P<0.001, P<0.05, P<0.05). Tests show that the polymorph form P has better antidepressant effect. Referring to the forced swimming test of the polymorph form P mentioned above, forced swimming tests of polymorph forms F, O, B and J are respectively conducted. Different from the forced swimming test of the polymorph form P, the test reagent is prepared by replacing the polymorph form P with the polymorph form F, O, B or J, and other operations are the same as the forced swimming test described above. The obtained results are consistent with the results of polymorph form P aqueous solution. The polymorph forms F, O, B and J can effectively reduce the static times and duration of forced swimming in rats, increase the swimming times and duration of rats, and increase the wall climbing times and duration.

The present disclosure is an example of principles of embodiments of the present application, and is not intended to limit the present application in any form or substance, or to limit the present application to specific embodiments. It is obvious to those skilled in the art that the elements, compounds, polymers, components, compositions, preparations, process methods and the like of the technical scheme of the embodiments of the present application can be varied, changed, modified and evolved without departing from the principles, spirit and scope of the embodiments and technical schemes of the present application as defined in the claims as described above. These variations, changes, modifications and evolved embodiments are all included in the equivalent embodiments of this application, and these equivalent embodiments are all included in the scope of this application defined by the claims. Although embodiments of the present application may be embodied in many different forms, some embodiments of the present invention are described in detail herein. In addition, embodiments of the present application include any possible combination of some or all of the various embodiments described herein, and are also included within the scope of the present application as defined by the claims. All patents, patent applications and other cited materials mentioned anywhere in this application or in any one of the cited patents, cited patent applications or other cited materials are hereby incorporated by reference in their entirety.

The above disclosure is intended to be illustrative rather than exhaustive. For those skilled in the art, this specification will suggest many variations and alternatives. All such alternatives and variations are intended to be included within the scope of the present claims, wherein the term "including" means "including, but not limited to".

The description of alternative embodiments of the present invention has been completed herein. Those skilled in the art will recognize other equivalent transformations of the embodiments described herein, which are also encompassed by the claims appended hereto.

INDUSTRIAL PRACTICABILITY

Five polymorph forms B, P, F, J and O of (4-((R)-((2S,5R)-4-(3-fluorobenzyl)-(2,5-dimethylpiperazine-1-yl)(3-hydroxyphenyl)methyl)phenyl)(4-methylpiperidine-1-yl) methanone dihydrochloride provided by embodiments of the invention have high solubility, good absorption, high bioavailability, low toxicity and good stability, can effectively prevent and treat depression and other potential diseases, and are suitable for the development and industrial production of new drugs. In addition, the preparation method of the five polymorph forms provided by the embodiments of the invention is simple and feasible, and is suitable for industrial production.

What we claim is:

1. A polymorph form P of (4-((R)-((2S,5R)-4-(3-fluorobenzyl)-(2,5-dimethylpiperazine-1-yl) (3-hydroxyphenyl) methyl)phenyl)(4-methylpiperidine-1-yl) methanone dihydrochloride, wherein an X-ray powder diffraction pattern of the polymorph form P comprises the following diffraction peaks at 2θ value: 10.0±0.2°, 9.1±0.2°, 21.3±0.2°, 22.6±0.2° and 14.5±0.2°.

2. The polymorph form P of claim 1, wherein the X-ray powder diffraction pattern of the polymorph form P further comprises any one or more of diffraction peaks at 2θ value selected from 17.7±0.2°, 20.8±0.2°, 13.8±0.2°, 23.1±0.2°, 24.9±0.2°, 27.0±0.2°, 27.8±0.2°, 18.4±0.2°, 12.7±0.2°, 16.6±0.2°, 31.1±0.2°, 11.5±0.2° and 28.2±0.2°.

3. The polymorph form P of claim 1, wherein the melting point of the polymorph form P measured by differential scanning calorimetry is in the range of 180.7° C. to 188.5° C.

4. The polymorph form P of claim 1, wherein the polymorph form P has an XRPD pattern shown in FIG. 5 and TGA and DSC patterns shown in FIG. 6.

5. A preparation method of a polymorph form P of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, wherein an X-ray powder diffraction pattern of the polymorph form P comprises the following diffraction peaks at 2θ value: 10.0±0.2°, 9.1±0.2°, 21.3±0.2°, 22.6±0.2° and 14.5±0.2°, and the method comprises following process:

process (1): adding a solvent to (4-((R)-((2S,5R)-4-(3-fluorobenzyl)-(2,5-dimethylpiperazine-1-yl) (3-hydroxyphenyl)methyl)phenyl)(4-methylpiperidine-1-yl) methanone, then adding a concentrated hydrochloric acid solution, stirring until no solid precipitates, filtering and drying to obtain the polymorph form P; or process (2): adding a solvent to a polymorph form B of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride, stirring until the dissolution equilibrium is reached, and separating solid to obtain the polymorph form P; wherein an X-ray powder diffraction pattern (XRPD) of the polymorph form B comprises the following diffraction peaks at 2θ value: 17.6±0.2°, 8.0±0.2°, 23.6±0.2°, 13.0±0.2° and 9.2±0.2°; or process (3): adding a solvent to a polymorph form F of (4-((R)-((2S,5R)-4-(3-fluorobenzyl)-(2,5-dimethylpiperazine-1-yl)(3-hydroxyphenyl)methyl)phenyl)(4-methylpiperidine-1-yl)methanone dihydrochloride to obtain a suspension, stirring until the dissolution equilibrium is reached, separating solid to obtain the polymorph P; wherein an X-ray powder diffraction pattern of the polymorph form F comprises the following diffraction peaks at 2θ value: 23.7±0.2°, 14.6±0.2°, 11.8±0.2°, 13.0±0.2° and 17.2±0.2°;

wherein, in the processes (1) to (3), the solvent is selected from a group consisting of any one or more of acetonitrile, dimethylformamide, diethylacetamide, formamide, dichloromethane, dimethylsulfoxide, and tetrahydrofuran, a mixed solvent of dimethylsulfoxide with water, or a mixed solvent of dimethylformamide with water.

6. The preparation method of claim 5, wherein the process (1) further comprises the step of adding the polymorph form P as a seed crystal to the reaction after adding the concentrated hydrochloric acid solution.

7. The preparation method of claim 6, wherein the mass of the polymorph form P serving as the seed crystal is 1% to 20% of the mass of (4-((R)-((2S,5R)-4-(3-fluorobenzyl)-(2,5-dimethylpiperazine-1-yl)(3-hydroxyphenyl)methyl) phenyl) (4-methylpiperidine-1-yl)methanone.

8. The preparation method of claim 5, wherein in process (1), for 10 g of the (4-((R)-((2S,5R)-4-(3-fluorobenzyl)-(2,5-dimethylpiperazin-1-yl)(3-hydroxyphenyl)methyl)phenyl) (4-methylpiperidine-1-yl)methanone, the amount of solvent added is 50 mL to 1000 mL, and the amount of the concentrated hydrochloric acid solution added is 1.5 mL to 7.0 mL, the stirring is carried out in the range of 40° C. to 60° C.; and the time for stirring is 0.5 h to 12 h.

9. The preparation method of claim 5, wherein in process (2), for 1.5 g of the polymorph form B, the amount of solvent added is 20 mL to 500 mL, the stirring reaction is carried out in the range of 40° C. to 60° C., and the stirring reaction is carried out for 1 h to 12 h.

10. The preparation method of claim 5, wherein in process (3), for 1.5 g of the polymorph form F, the amount of solvent added is 20 mL to 500 mL, the stirring reaction is carried out in the range of 10° C. to 40° C., and the time for the stirring reaction is 1 h to 5 day.

11. A pharmaceutical composition comprising of the polymorph form P of claim 1 and a pharmaceutically acceptable carrier or excipient.

12. The preparation method of claim 5, wherein the X-ray powder diffraction pattern of the polymorph form B further comprises any one or more of diffraction peaks at 2θ value selected from 19.8±0.2°, 15.6±0.2°, 14.6±0.2°, 25.4±0.2°, 11.7±0.2°, 26.7±0.2°, 19.4±0.2°, 22.5±0.2°, 16.8±0.2° and 18.4±0.2°.

13. The preparation method of claim 5, wherein the melting point of the polymorph form B measured by differential scanning calorimetry is in the range of 154.4° C. to 171.6° C.

14. The preparation method of claim 5, wherein the polymorph form B has the XRPD pattern shown in FIG. 1 and TGA and DSC patterns shown in FIG. 2.

15. The preparation method of claim 5, wherein the X-ray powder diffraction pattern of the polymorph form F further comprises any one or more of diffraction peaks at 2θ value selected from 27.8±0.2°, 13.4±0.2°, 19.7±0.2°, 8.7±0.2°, 7.8±0.2°, 26.2±0.2°, 15.7±0.2°, 21.5±0.2° and 9.4±0.2°.

16. The preparation method of claim 5, wherein the melting point of the polymorph form F measured by differential scanning calorimetry is in the range of 179.1° C. to 185.9° C.

17. The preparation method of claim 5, wherein the polymorph form F has an XRPD pattern shown in FIG. 3 and TGA and DSC patterns shown in FIG. 4.

* * * * *